(12) United States Patent
Fujita et al.

(10) Patent No.: US 8,251,447 B2
(45) Date of Patent: Aug. 28, 2012

(54) BIO-SIGNAL ANALYZER, SEAT AND BIO-SIGNAL ANALYZING METHOD

(75) Inventors: Etsunori Fujita, Hiroshima (JP); Yumi Ogura, Hiroshima (JP); Naoki Ochiai, Hiroshima (JP); Shinichiro Maeda, Hiroshima (JP); Shigeki Wagata, Hiroshima (JP)

(73) Assignee: Delta Tooling Co., Ltd., Hiroshima-shi (JP)

( * ) Notice: Subject to any disclaimer, the term of this patent is extended or adjusted under 35 U.S.C. 154(b) by 375 days.

(21) Appl. No.: 12/527,205

(22) PCT Filed: Oct. 25, 2007

(86) PCT No.: PCT/JP2007/070786
§ 371 (c)(1),
(2), (4) Date: Nov. 23, 2009

(87) PCT Pub. No.: WO2008/099537
PCT Pub. Date: Aug. 21, 2008

(65) Prior Publication Data
US 2010/0117411 A1    May 13, 2010

(30) Foreign Application Priority Data
Feb. 14, 2007 (JP) .................................. 2007-034144

(51) Int. Cl.
*A47C 4/54* (2006.01)
(52) U.S. Cl. ............. 297/284.6; 297/284.13; 297/284.3; 297/217.2
(58) Field of Classification Search .... 297/284.1–284.3, 297/284.6, 284.9, 217.2, 217.3
See application file for complete search history.

(56) References Cited

U.S. PATENT DOCUMENTS 4,204,657 A * 5/1980 Graham ................... 244/122 R
4,580,837 A * 4/1986 Bayley ..................... 297/362.12
(Continued)

FOREIGN PATENT DOCUMENTS
JP          9 308614        12/1997
(Continued)

OTHER PUBLICATIONS
U.S. Appl. No. 13/059,904, filed Feb. 18, 2011, Fujita, et al.
(Continued)

*Primary Examiner* — Laurie Cranmer
(74) *Attorney, Agent, or Firm* — Oblon, Spivak, McClelland, Maier & Neustadt, L.L.P.

(57) ABSTRACT

There are provided a bio-signal analyzer using a sensor capable of detecting, even though it is non-invasive, a more prominent bio-signal, and a seat using the bio-signal analyzer. Air cushions (10), which are sensors detecting a bio-signal in a non-invasive manner, are disposed at the positions corresponding respectively to left and right iliocostalis lumborum muscles of a person, in a substantially vertically long state along the iliocostalis lumborum muscles, with upper ends thereof being set at least at the height corresponding to a lower face of a human diaphragm. In the diaphragm, bio-signals such as heartbeats, breaths, or pulsations of aorta passing through the vicinity of the diaphragm are resonated and amplified. Further, the iliocostalis lumborum muscles are at positions where they are easily vibrated by pulsations of aorta passing through the vicinity of the lumbar region. Therefore, by disposing the air cushions (10) as described above, bio-signals amplified by the diaphragm and the iliocostalis lumborum muscles can be detected.

12 Claims, 29 Drawing Sheets

U.S. PATENT DOCUMENTS

| | | | |
|---|---|---|---|
| 4,759,543 A * | 7/1988 | Feldman | 482/148 |
| 5,127,708 A * | 7/1992 | Kishi et al. | 297/284.1 |
| 5,469,592 A * | 11/1995 | Johnson | 5/654 |
| 5,523,664 A | 6/1996 | Ogasawara | 318/590 |
| 5,574,641 A * | 11/1996 | Kawakami et al. | 701/1 |
| 6,012,188 A * | 1/2000 | Daniels et al. | 5/654 |
| 6,220,667 B1 * | 4/2001 | Wagner | 297/391 |
| 6,592,184 B1 * | 7/2003 | Segal et al. | 297/284.6 |
| 7,015,818 B2 | 3/2006 | Takashima | |
| 7,093,898 B2 * | 8/2006 | Ladron De Guevara | 297/284.6 |
| 7,113,100 B2 * | 9/2006 | Yoshinori et al. | 340/575 |
| 7,134,718 B2 * | 11/2006 | Yasuda et al. | 297/216.13 |
| 7,152,920 B2 * | 12/2006 | Sugiyama et al. | 297/284.6 |
| 7,172,247 B2 * | 2/2007 | Beloch et al. | 297/284.7 |
| 7,275,793 B2 * | 10/2007 | Fujita et al. | 297/452.56 |
| 7,532,964 B2 * | 5/2009 | Fujita et al. | 701/36 |
| 7,717,520 B2 * | 5/2010 | Boren et al. | 297/452.48 |
| 7,905,548 B2 * | 3/2011 | Gupta et al. | 297/284.9 |
| 2004/0236235 A1 | 11/2004 | Fujita et al. | |
| 2007/0078351 A1 | 4/2007 | Fujita et al. | |
| 2007/0299636 A1 | 12/2007 | Fujita et al. | |

FOREIGN PATENT DOCUMENTS

| | | |
|---|---|---|
| JP | 10 146321 | 6/1998 |
| JP | 2001 276020 | 10/2001 |
| JP | 2002 187450 | 7/2002 |
| JP | 2004 344612 | 12/2004 |
| JP | 2005 152310 | 6/2005 |
| JP | 2005 168608 | 6/2005 |
| JP | 2006 42904 | 2/2006 |
| JP | 2007 90032 | 4/2007 |
| WO | 2005 039415 | 5/2005 |
| WO | 2005 092193 | 10/2005 |

OTHER PUBLICATIONS

Maeda, Shinichiro et al., "Measurement method of Biological Signal from the Hips", Preprints of Meeting on Automotive Engineers, No. 78-06, pp. 9 to 12, (2006) (with English abstract).

U.S. Appl. No. 13/266,188, filed Oct. 25, 2011, Fujita, et al.

U.S. Appl. No. 13/321,367, filed Nov. 18, 2011, Fujita, et al.

\* cited by examiner

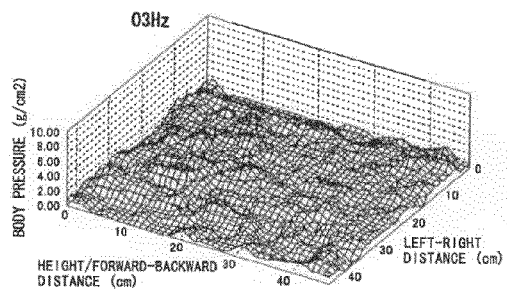
FIG. 10A 03Hz
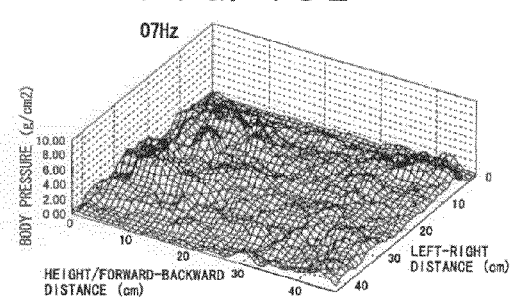
FIG. 10E 07Hz
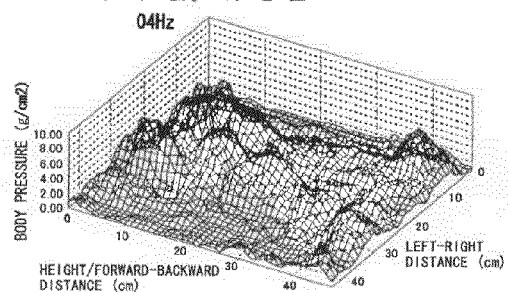
FIG. 10B 04Hz
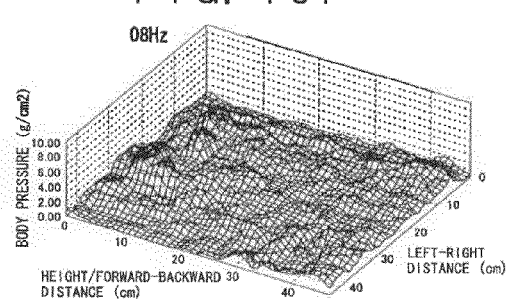
FIG. 10F 08Hz
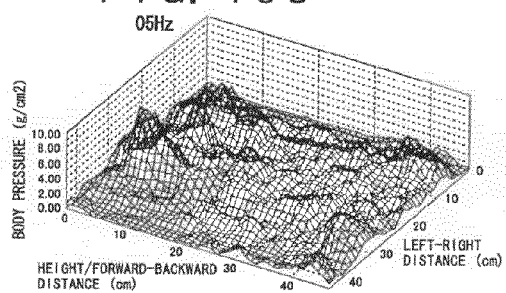
FIG. 10C 05Hz
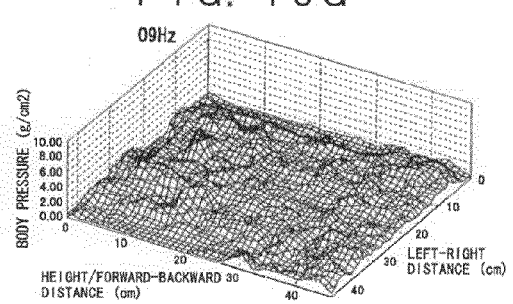
FIG. 10G 09Hz
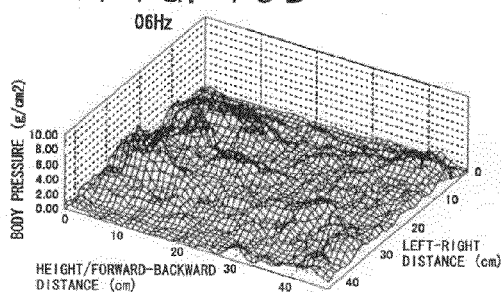
FIG. 10D 06Hz
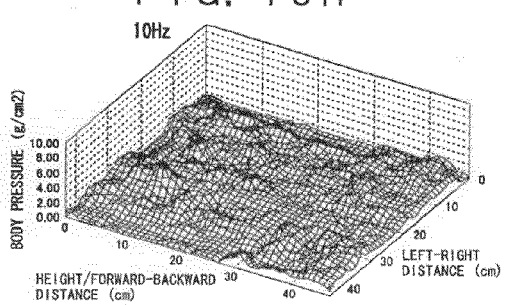
FIG. 10H 10Hz F I G. 1 2 A
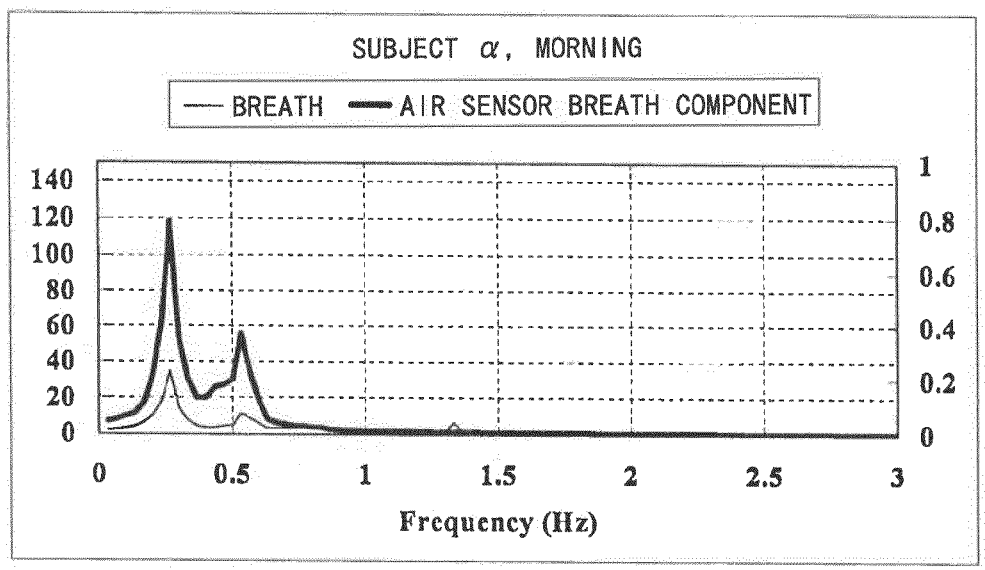
F I G. 1 2 B
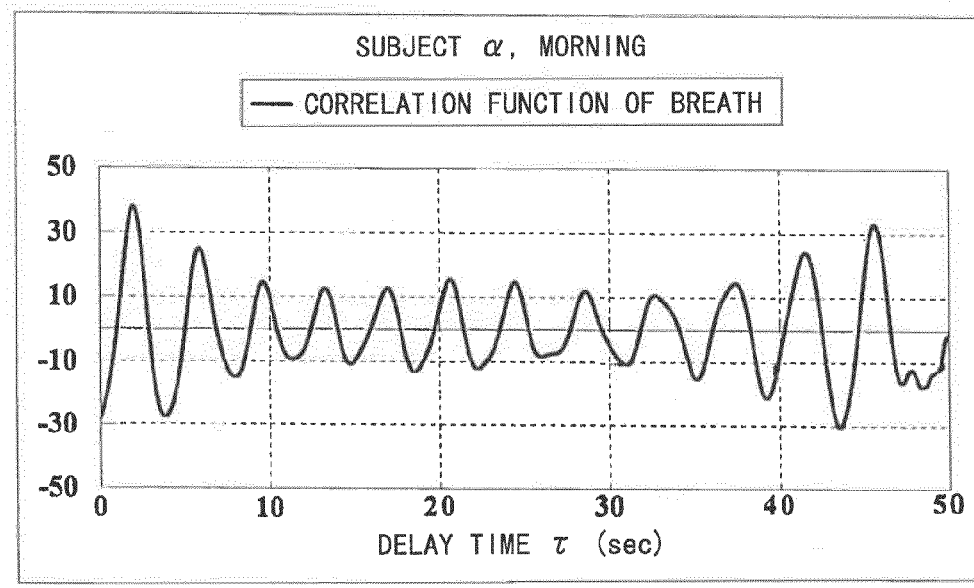

ORIGINAL WAVEFORM

CHANGE OF VOICE SPECTRUM

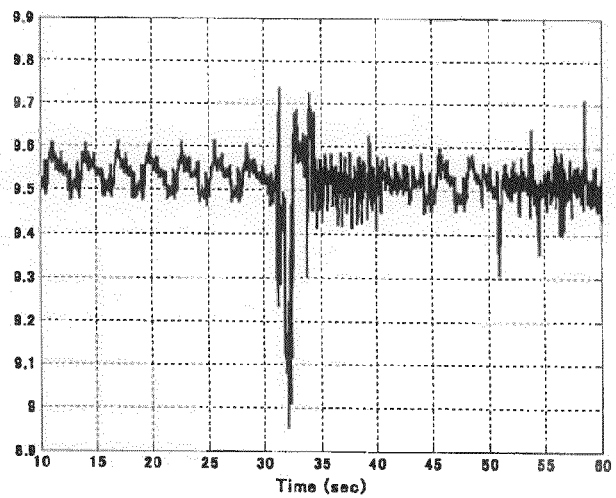
F I G. 20 A
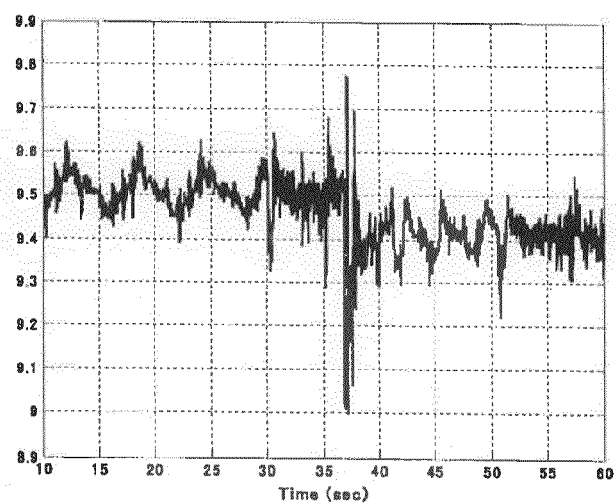
F I G. 20 B
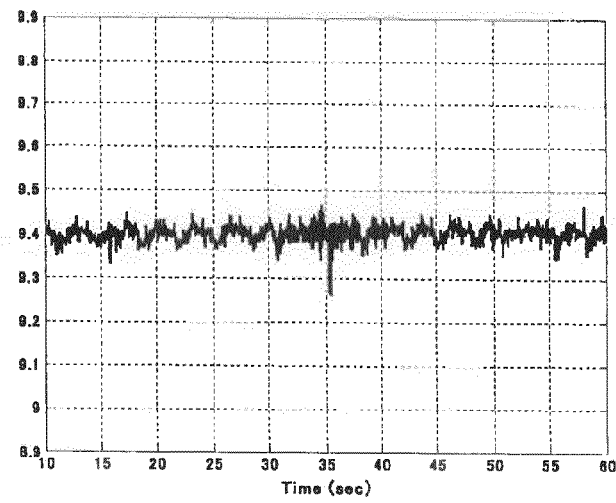
F I G. 20 C

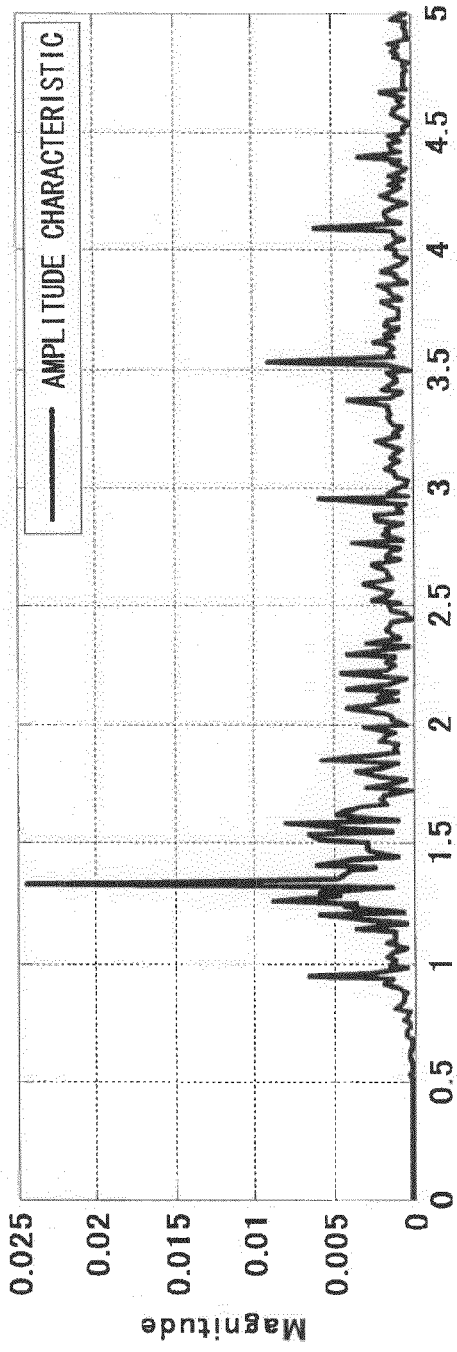
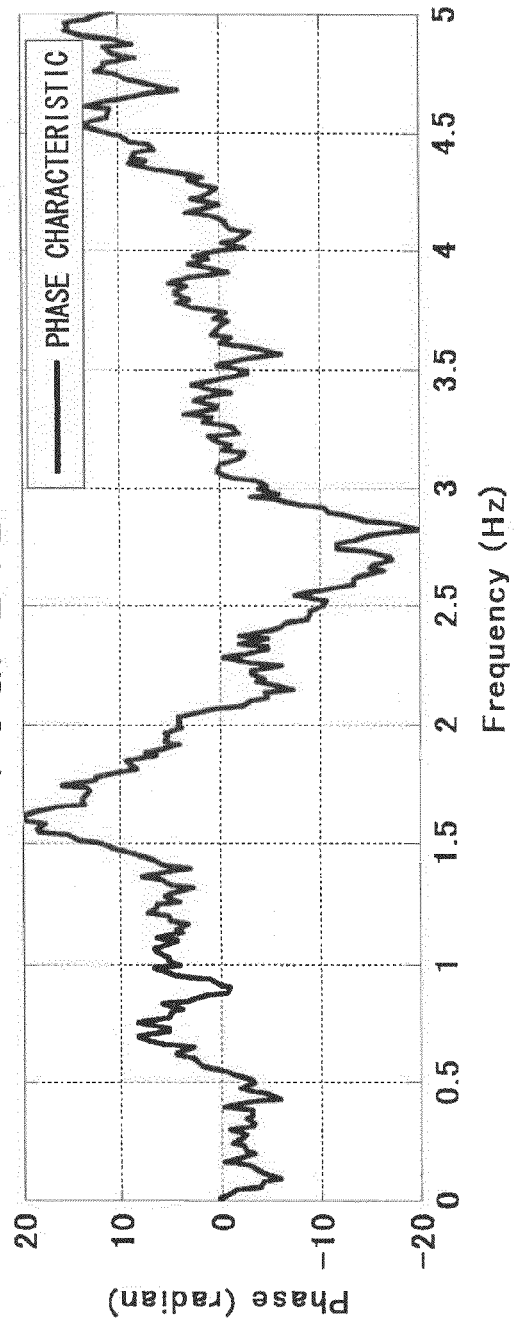

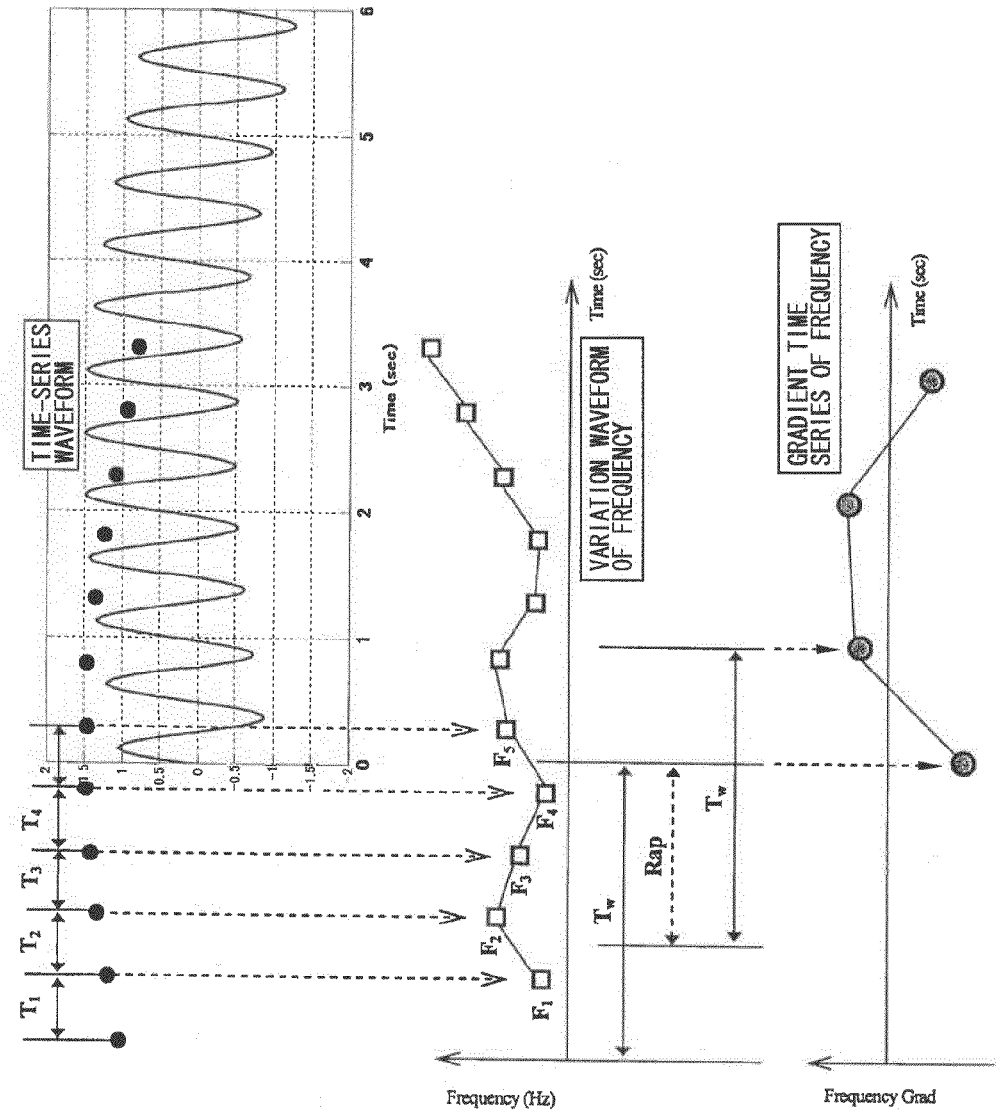

FIG. 26
(MORNING)
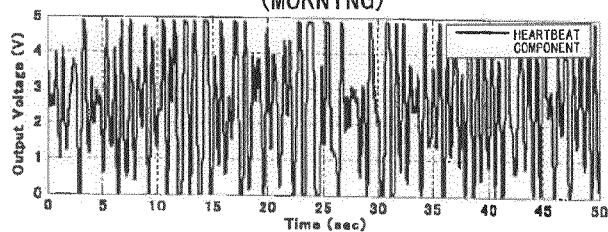
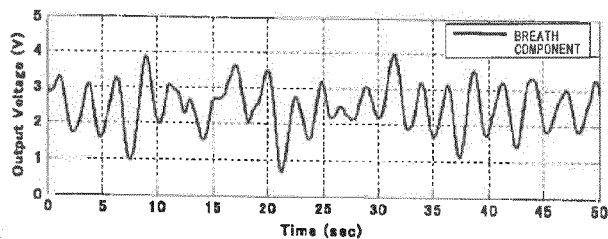
(NOON)
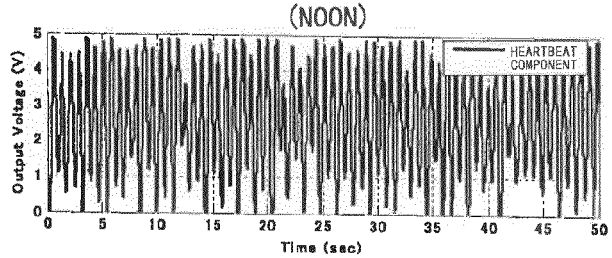
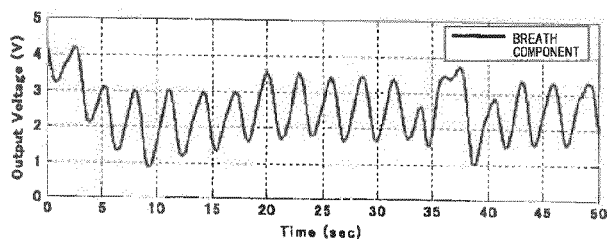
(NIGHT)
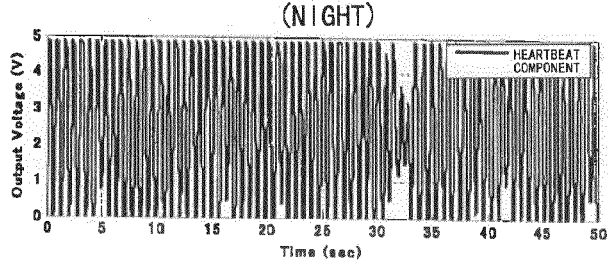
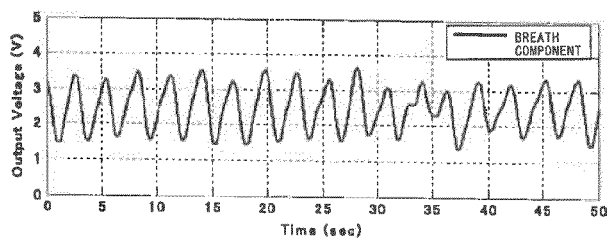

FIG. 27
(MORNING)
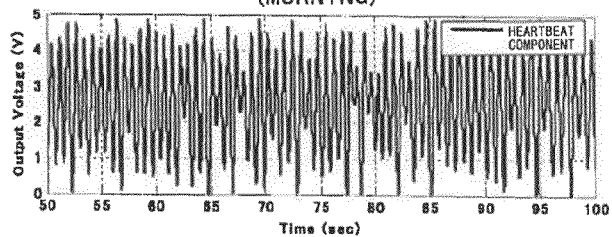
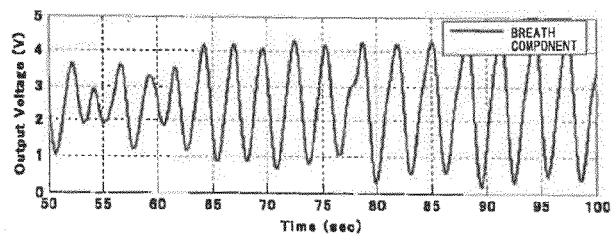
(NOON)
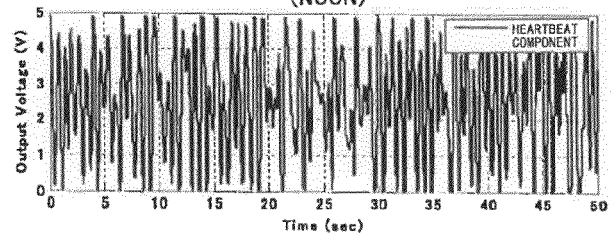
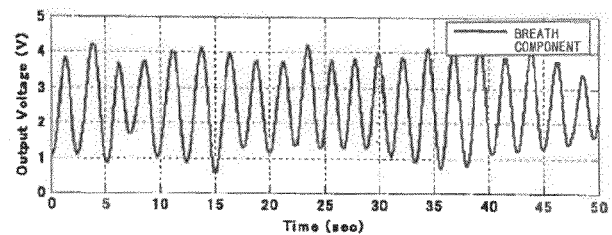
(NIGHT)
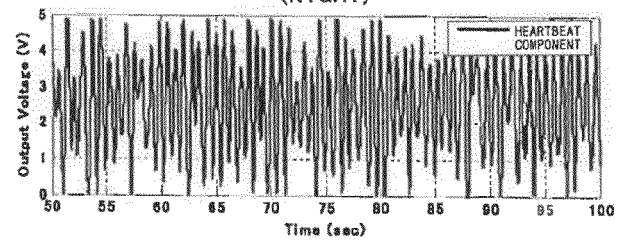
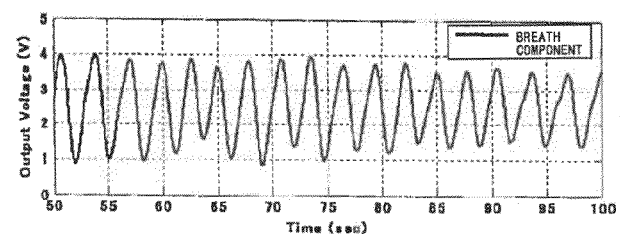

FIG. 28
(MORNING)
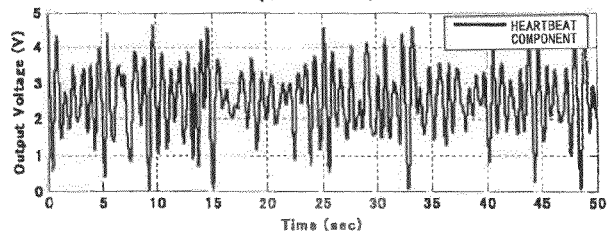
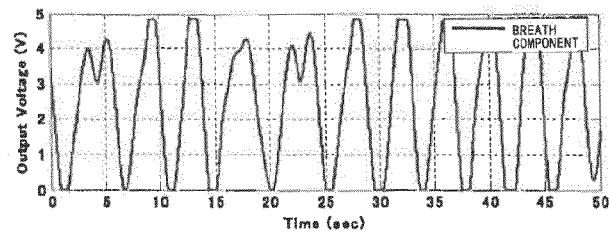
(NOON)
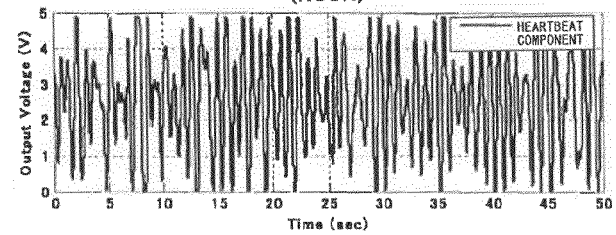
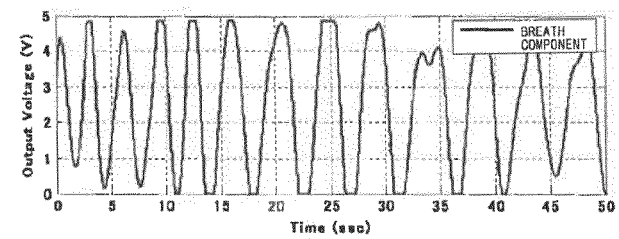
(NIGHT)
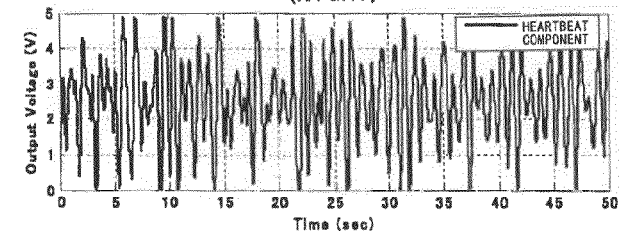
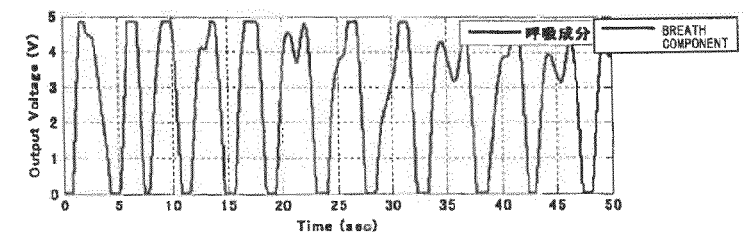

BIO-SIGNAL ANALYZER, SEAT AND BIO-SIGNAL ANALYZING METHOD

TECHNICAL FIELD

The present invention relates to a technique for detecting a bio-signal to analyze the condition of a human body, and particularly relates to a bio-signal analyzer using air cushions capable of detecting a bio-signal non-invasively, a seat using the bio-signal analyzer, and a bio-signal analyzing method.

BACKGROUND ART

In late years, monitoring the human condition of a driver while driving has been drawing attention as a measure for preventing a traffic accident. For example, Patent Documents 1 to 3 disclose a technique to detect vibration on a body surface accompanying beating of the heart with a piezoelectric element (piezoelectric film sensor) in a thin film form attached to a cushion material forming a seat cushion. This technique is to monitor the human condition by chaos analysis of output of the piezoelectric element and does not require attaching of a large monitoring device to the head, allowing easy evaluation of the human condition of a driver.

Patent Document 1: Japanese Patent Application Laid-open No. H9-308614
Patent Document 2: Japanese Patent Application Laid-open No H10-146321.
Patent Document 3: Japanese Patent Application Laid-open No2005-168608.

DISCLOSURE OF THE INVENTION

Problems to be Solved by the Invention

The technique disclosed in Patent Documents 1 to 3 is to detect very small, minute vibration on the skin surface of buttocks transmitted accompanying heartbeats and breaths, and requires highly sensitive sensors. Particularly while idling or traveling, there is large influence of vibration (noise signal) due to external factors inputted via the vehicle body. For clear distinction from noise signals, for example in WO2005/092193, the applicants have proposed to obtain time-series data of a gradient of an amplitude change ratio (gradient of a power value), which is obtained by obtaining the rate of change of displacement (amplitude) of a bio-signal and further performing slide calculation of the rate of change a predetermined number of times at a predetermined slide overlap rate, or obtain time-series data of a maximum Lyapunov index gradient, which is obtained by similarly performing slide calculation of the maximum Lyapunov index of a chaos indicator. The respective time-series data of gradients obtained as above allow actualization of fluctuating waveform data (data of biological fluctuation) peculiar to bio-signals, and thereby many noise signals can be cut off. Such an approach by the applicants has an advantage that minute non-invasively measured bio-signals can be extracted, but the bio-signals detected with sensors are desired to be more prominent signals than minute signals.

The present invention is made in consideration of the foregoing situation, and an object thereof is to provide a bio-signal analyzer using a sensor capable of detecting a prominent bio-signal in a non-invasive manner just by seating, a seat using the bio-signal analyzer, and a bio-signal analyzing method. Further, another object of the invention is to provide a bio-signal analyzer which allows to increase body supportability by disposing this sensor and thereby increase body pressure dispersibility, and a seat using this bio-signal analyzer.

Means for Solving the Problems

To solve the above-described problems, a bio-signal analyzer of the present invention includes an air cushion having an air bag formed by sealing except an air inlet/outlet port and a resilience applying member, which applies resilience in an expansion direction to the air bag when air is exhausted from the inlet/outlet port by pressing with a load, and allows air to enter the air bag through the inlet/outlet port accompanying decrease of the load, the air cushion being incorporated in a portion supporting a vicinity of the lumbar region of a person in a human body support means, and an analyzing means analyzing a human condition from an air pressure variation in the air cushion generated by a human bio-signal. The air cushion is disposed at least at one of positions corresponding respectively to left and right iliocostalis lumborum muscles of a person, in a substantially vertically long state along the iliocostalis lumborum muscles, and has a length allowing to set an upper end thereof at least at a height corresponding to a lower face of a human diaphragm.

Preferably, the length of the air cushion is in a range of 150 mm to 300 mm.

Preferably, the resilience applying member is made of a resilient member which is accommodated in the air bag and applies resilience to the air bag from inside, and the resilient member is formed of a three-dimensional solid knitted fabric.

Further, preferably, the air cushion includes two air bags, and has a structure using the two air bags overlapping each other. In this case, preferably, the analyzing means is configured to perform analysis using a sum of values of respective air pressure variations of the two air bags of the air cushion.

Furthermore, a seat of the present invention includes air cushions incorporated in a portion supporting a vicinity of a lumbar region in a seat back. The air cushions each include an air bag formed by sealing except an air inlet/outlet port and a resilience applying member, which applies resilience in an expansion direction to the air bag when air is exhausted from the inlet/outlet port by pressing with a load, and allows air to enter the air bag through the inlet/outlet port accompanying decrease of the load. The air cushions are disposed at least at one of positions corresponding respectively to left and right iliocostalis lumborum muscles of a person, in a substantially vertically long state along the iliocostalis lumborum muscles, with upper ends thereof being set at least at a height corresponding to a lower face of a human diaphragm. The air cushions allow to detect an air pressure variation in the air cushions generated by a human bio-signal so as to analyze a human condition.

Preferably, the length of the air cushions used in the seat is in a range of 150 mm to 300 mm.

Further, preferably, the air cushions are disposed so that respective inside lower ends of the air cushions are located in ranges of 20 mm to 80 mm leftward and rightward respectively from a center of the seat back forming the seat and in a range of 10 mm to 80 mm upward along the seat back from a boundary between a seat cushion and the seat back.

Further, preferably, the air cushions are disposed so that respective inside upper ends of the air cushions are located in ranges of 40 mm to 100 mm leftward and rightward respectively from the center of the seat back and separated from the center of the seat back farther than the inside lower ends.

Further, preferably, the resilience applying member used in the seat is made of a resilient member which is accommodated in the air bag and applies resilience to the air bag from inside, and the resilient member is formed of a three-dimensional solid knitted fabric. Further, preferably, the air cushions each include two air bags, and have a structure using the two air bags overlapping each other. In this case, preferably, the analyzing means is configured to perform analysis using a sum of values of respective air pressure variations of the two air bags of the air cushions.

Further, preferably, the seat further includes an analyzing means analyzing a human condition from air pressure variation data in the air cushions generated by a human bio-signal, the analyzing means attached to a portion of one of the seat cushion and the seat back.

Furthermore, the present invention provides a bio-signal analyzing method using an air cushion incorporated in a portion supporting a vicinity of a lumbar region in a seat back, the method including:

using as the air cushion an air cushion having an air bag formed by sealing except an air inlet/outlet port and a resilience applying member, which applies resilience in an expansion direction to the air bag when air is exhausted from the inlet/outlet port by pressing with a load, and allows air to enter the air bag through the inlet/outlet port accompanying decrease of the load;

setting the air cushion at least at one of positions corresponding respectively to left and right iliocostalis lumborum muscles of a person, in a substantially vertically long state along the iliocostalis lumborum muscles, with upper ends thereof being at least at a height corresponding to a lower face of a human diaphragm; and detecting an air pressure variation in the air cushion generated by a breath, a heartbeat or a voice.

Preferably, the above method of the present invention further includes detecting an air pressure variation in the air cushion generated by a voice, so as to determine a human condition.

Preferably, the above method of the present invention further includes detecting an air pressure variation in the air cushion generated by a breath, so as to determine a state of a heartbeat.

Effect of the Invention

In the present invention, air cushions, which are sensors detecting a bio-signal in a non-invasive manner, are disposed at least at one of the positions corresponding respectively to left and right iliocostalis lumborum muscles of a person, in a substantially vertically long state along the iliocostalis lumborum muscles, with upper ends thereof being set at least at the height corresponding to a lower face of a human diaphragm. In the diaphragm, bio-signals such as heartbeats, breaths, or pulsations of aorta passing through the vicinity of the diaphragm are resonated and amplified. Further, the iliocostalis lumborum muscles are at positions where they are easily vibrated by pulsations of aorta passing through the vicinity of the lumbar region. Therefore, with the air cushions being disposed as described above, by just sitting on the seat, it becomes possible to use the diaphragm and the iliocostalis lumborum muscles to detect bio-signals amplified by them, without putting on any kind of measuring device on the body.

Of course, for example, when it is arranged to set a piezoelectric element or the like to a position close to the heart of the person, the detection sensitivity to heartbeats or the like increases. But in this case, a dedicated sensor for detecting a bio-signal must be arranged. For example, when such a sensor is arranged at a position corresponding to the heart in the case of a vehicle seat, it is necessary to separately provide a member needed in terms of functions of the seat, such as a lumbar support. In contrast, in the present invention, by disposing the air cushions in a substantially vertically long state along the iliocostalis lumborum muscles, the air cushions are able to function as a bio-signal detection sensor while having the function as a lumbar support to support the lumbar region. Moreover, using the resonating function of the diaphragm and the vibrating function of the iliocostalis lumborum muscles, a bio-signal can be detected with high sensitivity. That is, a breath, a heartbeat, a voice, or the like is transmitted to the air cushions as solid propagation is sound via the diaphragm and other muscles. The solid propagation sound at this time resonates, with its pressure value and frequency, the air bags of the air cushions having predetermined surface rigidity, and further vibrates connecting fibers of three-dimensional solid knitted fabrics which are resilient members arranged therein, thereby vibrating air in the air bags to generate an air pressure variation, or pressing the air cushions to generate an air pressure variation. Thus, a bio-signal can be detected by measuring the air pressure variation generated in this manner. In particular, in the case of a voice signal, when a human voice propagates through the air, it is at a high frequency of several hundred Hz to several kHz and a dedicated device is needed to sample the voice signal. With the present invention, since the air cushions are provided along the iliocostalis lumborum muscles as described above, the voice signal can be sampled as vibration at lower frequency as solid propagation sound via the diaphragm and other muscles than the air propagation sound. The degree of tension of muscles changes between a tense mental and physical state and a relaxed mental and physical state. Accordingly, also with a voice propagating the diaphragm and other muscles, the vibration of these muscles changes depending on whether in a tense state or not. Therefore, it is possible to presume the state of the nervous system of a sitter (driver) by detecting a voice. Further, with the present invention, the heartbeat can be measured directly, but when it is hindered by vibration inputted from the outside when the automobile is traveling, the state of heartbeat variation can be estimated from the air pressure variation by breathing.

Further, since the air cushions are arranged respectively to the positions corresponding to the iliocostalis lumborum muscles of a human body, the vicinity of a body side of the lumbar region is supported, and the posture thereof becomes stable. Moreover, since the air cushions fit the shape of the lumbar region, the body pressure dispersibility increases, and the vibration absorbing characteristic and the seating comfort improve.

BRIEF DESCRIPTION OF DRAWINGS

FIGS. 10A to 10H are graphs showing body pressure distributions in a seat back part of a seat having a conventional structure with respect to frequencies from 3 Hz to 10 Hz;

FIG. 11 are graphs showing results of test example 1, where

FIG. 12 are graphs showing results of test example 1, where FIG. 12A shows a spectral waveform of breath components obtained from a distortion type respirometer and a spectral waveform of breath components obtained from the air cushions, and FIG. 12B shows a correlation function of them;

FIG. 13 are graphs showing results of test example 2, where

FIG. 14 are graphs showing results of test example 2, where

FIG. 15 are graphs showing results of test example 3, where

FIG. 18 are graphs showing results of verification of effectiveness of bio-signal sampling when values of air pressure variations of air bags of the air cushions are addition processed and when they are subtraction processed, where

FIG. 20 shows time-series waveforms of voice signals of three subjects, where FIG. 20A shows a time-series waveform indicating a voice signal of a male in his thirties (middle to high voice), FIG. 20B shows a time-series waveform indicating a voice signal of a male in his twenties (low voice), FIG. 20C shows a time-series waveform indicating a voice signal of a female in her twenties (thin and high voice);

FIGS. 21A and 21B are graphs showing an amplitude characteristic (magnitude) and phase characteristic (θ) representing a frequency response function (TF) obtained in test example 6;

FIG. 22 shows graphs showing calculation of the gradient of a frequency relative to a time axis from time-series changes of the frequency relative to the time axis;

FIG. 26 shows graphs showing time-series waveforms of heartbeat components and breath components of one subject of test example 7 in the morning, at noon, and at night;

FIG. 27 shows graphs showing time-series waveforms of heartbeat components and breath components of another subject of test example 7 in the morning, at noon, and at night;

FIG. 28 shows graphs showing time-series waveforms of heartbeat components and breath components of still another subject of test example 7 in the morning, at noon, and at night;

Figure 1:
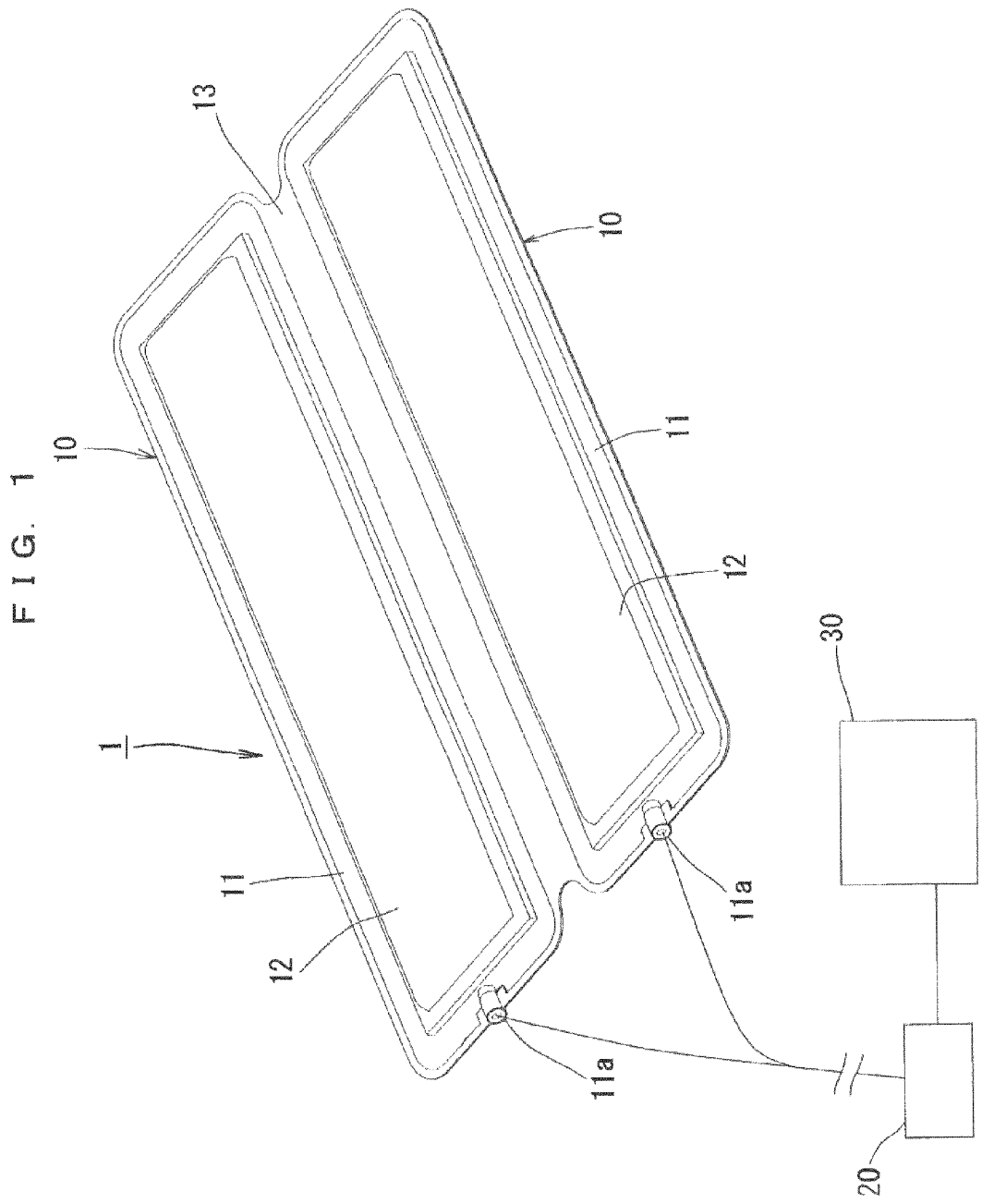
FIG. 1 is a view showing the structure of a bio-signal analyzer according to an embodiment of the present invention.

EXPLANATION OF NUMERALS AND SYMBOLS 1 bio-signal analyzer
10 air cushion
11 air bag
11a inlet/outlet port
12 resilience applying member
20 air pressure measuring instrument
30 analyzing means
100 seat
110 seat back
120 seat cushion
200 auxiliary cushion (cushion for seat)
210 seat back
220 seat cushion

BEST MODE FOR CARRYING OUT THE INVENTION

Figure 2:
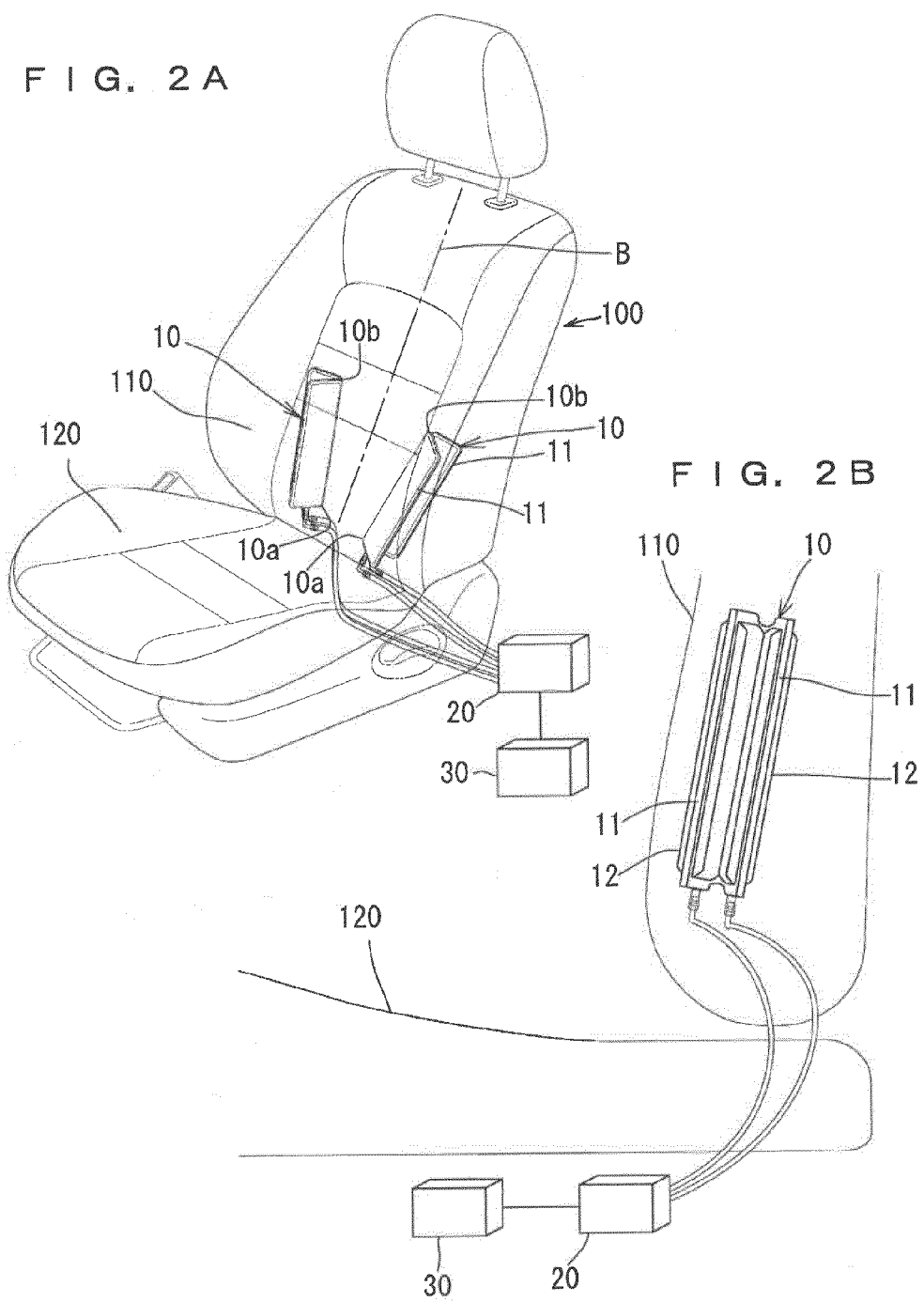
FIG. 2 is a view showing a state that the bio-signal analyzer according to the embodiment is incorporated in a seat.

Hereinafter, the present invention will be described in more detail based on embodiments of the invention shown in the drawings. FIG. 1 is a view showing a bio-signal analyzer 1 according to this embodiment. FIG. 2 is a view showing a state that this bio-signal analyzer 1 is applied to a seat 100. The bio-signal analyzer 1 has air cushions 10, an air pressure measuring instrument 20, and an analyzing means 30.

The air cushions 10 each have air bags 11 and a resilience applying member 12. The air bags 11 need to have rigidity required for solid propagation of a bio-signal and a human voice. This is because solid propagation sound attenuates when the rigidity is insufficient. Further, the air cushions 10 of this embodiment each include two air bags 11, 11 sandwiching a boundary portion 13, and as shown in FIG. 2, the two air bags 11, 11 in use are folded in two to overlap each other. The air bags 11, 11 are, as shown in FIG. 1, each formed in an arbitrary shape with a predetermined size, but preferably have a width of 40 mm to 100 mm and a length of 150 mm to 300 mm. Each air bag 11 is provided with an air inlet/outlet port 11a in an arbitrary portion, which is one end in a length direction in FIG. 1, and the other portion on the periphery is sealed entirely. The air pressure measuring instrument 20 is connected to the inlet/outlet port 11a. Thus, an air pressure variation is detected by the air pressure measuring instrument 20 when a load is applied to the air cushions 10 or when a load applied thereto decreases.

The air cushions 10 are incorporated in the vicinity of the lumbar region in a seat back 110. Specifically, in this embodiment, at the position corresponding to the left and right iliocostalis lumborum muscles of a person seated on the seat 100, the air cushions folded in two are disposed as shown in FIG. 2 in a substantially vertically long state along the iliocostalis lumborum muscles as described above. The iliocostalis lumborum muscles are located such that the distance between the iliocostalis lumborum muscles (that is, respective distances from the spine to the iliocostalis lumborum muscles) is shorter in a region closer to the buttocks than in a region closer to the diaphragm. Therefore, the substantially vertically long state means that the two air cushions 10, 10 are disposed slightly obliquely so that the gap therebetween becomes smaller downward with distance. Further, the air cushions 10, 10 have upper ends respectively set at least at the height corresponding to a lower face of the human diaphragm. To set the upper ends at least at the height corresponding to the lower face of the human diaphragm when disposed in the substantially vertically long state corresponding to the iliocostalis lumborum muscles, it is preferable that the air cushions 10, 10 each have a length of 150 mm to 300 mm as mentioned above. In addition, it is preferable that the upper ends of the air cushions 10, 10', when disposed at a highest position, are set not higher than the height corresponding to an upper face of the diaphragm.

To dispose the air cushions 10, 10 having a length in the range of 150 mm to 300 mm along the iliocostalis lumborum muscles with the upper ends being at least at the height corresponding to the lower face of the diaphragm, the air cushions 10, 10 just need to be disposed so that respective inside lower ends 10a, 10a of the air cushions 10, 10 are located in the ranges of 20 mm to 80 mm leftward and rightward respectively from the center B of the seat back 110 and in the range of 10 mm to 80 mm upward along the seat back 110 from the boundary between the seat cushion 120 and the seat back 110. Further, the air cushions 10, 10 are also disposed so that respective inside upper ends 10b, 10b thereof are located in the ranges of 40 mm to 100 mm leftward and rightward respectively from the center B of the seat back 110 and separated farther from the center B of the seat back 110 than the inside lower ends 10a, 10a.

The air bags 11 have a characteristic to resonate when solid propagation sound of a bio-signal of heartbeat, voice, breath, or the like is transmitted thereto via human muscles such as iliocostalis lumborum muscles. Accordingly, as described above, the air bags need to have high rigidity, and preferred to be a material having one or more gain of amplitude characteristic.

Figure 3:
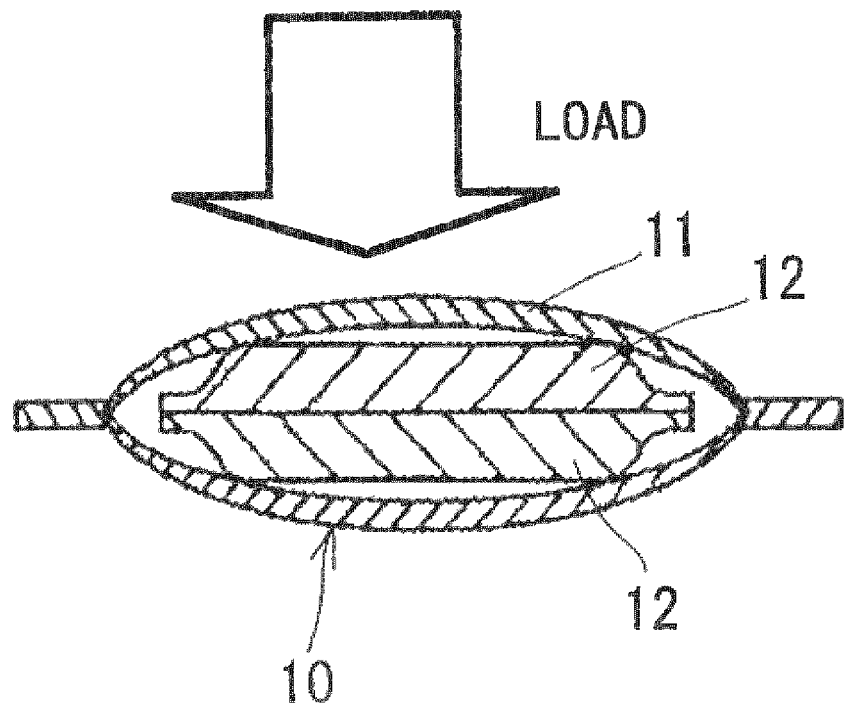
FIG. 3 is a cross-sectional view of one air bag forming an air cushion, and a resilience applying member accommodated in the air bag.

The resilience applying member 12 is formed to have a size that can be accommodated in each air bag 11, and applies resilience to each air bag 11 from the inside. For the resilience applying member 12, it is preferable to use a three-dimensional solid knitted fabric, by which high resilience can be obtained, and which exhibits a soft spring characteristic by a load concentrated at one point but exhibits a linear and rigid spring characteristic in a surface contact with a predetermined area, for example, a surface contact in the range of 98 mm diameter or larger corresponding to the diameter of a human buttock on one side. Due to having such characteristics, the three-dimensional solid knitted fabric has spring characteristics approximating to that of human muscles, which is relatively soft when locally pressed but is relatively rigid when pressed with a predetermined area. For accommodating in the air bag 11, for example, a strip-shaped three-dimensional solid knitted fabric having a width of about 10 mm to 90 mm and a length of about 80 mm to 280 mm is used. The resilience applying member 12 may be formed of one such strip-shaped three-dimensional solid knitted fabric, or as shown in FIG. 3, two such three-dimensional solid knitted fabrics in a layered state may be accommodated in the air bag 2.

The three-dimensional solid knitted fabric forming the resilience applying member 12 is knitted by reciprocating a connecting yarn between a pair of ground knitted fabrics positioned with a predetermined gap therebetween, and is formed in a predetermined shape using a double raschel knitting machine or the like. Here, the present invention attempts to capture a pulse wave flowing through a blood vessel by pumping of blood by the heart, a breath, or a voice as a pressure variation by solid propagation via muscles. In this situation, the resilience applying members 12 arranged in the air cushions 10, 10' repeat compression and restoration by this solid propagation. The fact that the three-dimensional solid knitted fabric has the spring characteristic approximating to that of human muscles means that the pressure (internal pressure) caused by vibration of actual human muscles and the pressure (external pressure) accompanying compression and restoration of the three-dimensional solid knitted fabric corresponding thereto are substantially equal, and it can be said that the measurement of air pressure variation in the air cushion 10 in the present invention is a technique using the principle of tonometry.

At this time, due to the pressure value and the frequency of solid propagation sound of a bio-signal, mainly a heartbeat or a voice for example, when transmitted as solid propagation sound to the air cushions 10 via muscles, operates to vibrate the air bags 11 since the air bags 11 of the air cushions 10 have predetermined rigidity. Also, due to the characteristics of the three-dimensional solid knitted fabric approximating to that of muscles, the vibration of the air bags 11 is transmitted to the connecting yarn of the three-dimensional solid knitted fabric, and this vibration operates so as to vibrate the air filled therein. As a consequence, a variation occurs in the air pressure measured via the inlet/outlet ports 11a of the air bags 11. On the other hand, depending on the pressure value and the frequency of solid propagation sound, for example a breath causes a pressure variation by compression or restoration of the air cushions 10 corresponding to movement of muscles accompanying the breath. Therefore, it is preferable that an overall load-displacement characteristic of the air cushions 10, including rigidity of the air bags 11 of the air cushions 10, approximates to a load-displacement characteristic of human muscles. This makes that human muscles and the air cushions 10 to be in an equilibrium state as described above, and tension that is about the same as that of human muscles works on the air cushions 10. Thus, the air cushions 10 respond sensitively to vibration of air due to the aforementioned solid propagation sound or movement of muscles, thereby allowing an amplified pressure variation to occur.

Incidentally, as the three-dimensional solid knitted fabric having characteristics approximating to human muscles, for example, the following ones can be used.

(1) Product number: 49076D (manufactured by Suminoe Textile Co., Ltd.)
Material:
Ground knitted fabric on the front side . . . 300 decitex/288f polyethylene terephthalate fiber temporary twisted finished yarn and 700 decitex/192f polyethylene terephthalate fiber temporary twisted finished yarn
Ground knitted fabric on the reverse side . . . a combination of 450 decitex/108f polyethylene terephthalate fiber temporary twisted finished yarn and 350 decitex/1f polytrimethylene terephthalate monofilament
Connecting yarn . . . 350 decitex/1f polytrimethylene terephthalate monofilament (2) Product number: 49013D (manufactured by Suminoe Textile Co., Ltd.)
Material:
Ground knitted fabric on the front side . . . two 450 decitex/108f polyethylene terephthalate fiber temporary twisted finished yarns
Ground knitted fabric on the reverse side . . . two 450 decitex/108f polyethylene terephthalate fiber temporary twisted finished yarns
Connecting yarn . . . 350 decitex/1f polytrimethylene terephthalate monofilament (3) Product number: 69030D (manufactured by Suminoe Textile Co., Ltd.)
Material:
Ground knitted fabric on the front side . . . two 450 decitex/144f polyethylene terephthalate fiber temporary twisted finished yarns
Ground knitted fabric on the reverse side . . . a combination of 450 decitex/144f polyethylene terephthalate fiber temporary twisted finished yarn and 350 decitex/1f polytrimethylene terephthalate monofilament
Connecting yarn . . . 350 decitex/1f polytrimethylene terephthalate monofilament (4) Product number: T24053AY5-1S manufactured by Asahi Kasei Fibers Corporation The air pressure measuring instrument 20 is connected to the inlet/outlet ports 11a of the air cushions 10 as described above. The air cushions 10 are disposed along the iliocostalis lumborum muscles from the positions corresponding to the diaphragm as described above. Thus, heartbeats, breaths, and pulsations are amplified by the diaphragm and the iliocostalis lumborum muscles and cause an air pressure variation in the air cushions 10 as described above. Incidentally, to detect the air pressure variation in the air cushions 10 more prominently, it is preferable that the air pressure measuring instrument 20 includes a differential transformer for amplifying the air pressure variation.

The electrical signal of the detected air pressure variation is sent to the analyzing means 30. The analyzing means 30 is made up of a computer in which a computer program analyzing output values of an air pressure variation so as to analyze the human condition is incorporated. Further, in this embodiment, as each air cushion 10, one having the two air bags 11, 11 bounded on the boundary portion 13 is used, and this air cushion is folded in two and incorporated in the seat 100. The air pressure variation is sampled from the two air bags 11, 11. The air pressure variation can be sampled with one air bag, but it is preferable to use, as in this embodiment, two overlapped air bags 11, 11 and use the sum obtained by adding the values of air pressure variations obtained from them. This addition provides a characteristic that, in the time-series waveforms of air pressure variations detected with the air bags 11, 11, the waveform of a bio-signal is emphasized in the region where the bio-signal is sampled, and vibration from the human body accompanying heartbeats, breaths, voices or the like can be sampled more precisely. Further, in this embodiment, air pressure variations are detected from the air cushions 10, 10 disposed on the left and right sides respectively. This is for responding to a situation that the seating position is deviated either leftward or rightward, where data with more excellent detecting sensitivity may be used out of data from the two air cushions 10, 10. Further, the average of the both can be adopted. The analyzing means 30 can be disposed by fixing at a position in the seat 100 where it does not hinder the function of the seat 100. Particularly, when the seat 100 is one for a vehicle, it becomes possible to know the human condition of the driver or the like while driving in real time, by fixing the analyzing means in the seat 100 or incorporating the analyzing means in an arbitrary portion of the vehicle body. When the bio-signal analyzer 1 of this embodiment is used for diagnosis purpose or the like, the air cushions 10 described above can, of course, be disposed in a chair, a bed or the like for diagnosing, and the analyzing means 30 can be made up of a laptop or desktop computer that is not fixed to the bed or the like.

Here, as the computer program set in the analyzing means 30, it is possible to use, for example, a program determining human conditions such as hypnagogic symptoms disclosed in WO2005/092193 proposed by the present applicants, a program quantizing the degree of fatigue disclosed in WO2005/039415, or the like. By these programs, hypnagogic symptoms or the degree of fatigue are determined.

TEST EXAMPLE

A subject was seated on the seat 100 for automobile having the bio-signal analyzer 1 as shown in FIG. 2, and a test of detecting bio-signals of the subject by air pressure variation was performed. The air cushion material 10 used in the test is one, as shown in FIG. 3, in which the resilience applying member 12 is fitted in the air bag 11. As the resilience applying member 12, there was used one in which two pieces of the three-dimensional solid knitted fabric with product number: T24053AY5-1S made by Asahi Kasei Fibers Corporation, with a thickness of 10 mm, a width of 40 mm, and a length of 220 mm, are overlapped and the peripheral portions thereof are vibration welded. The air bag 11 in which the resilience applying member 12 is fitted has dimensions of width of 50 mm and length of 230 mm.

Figure 4:
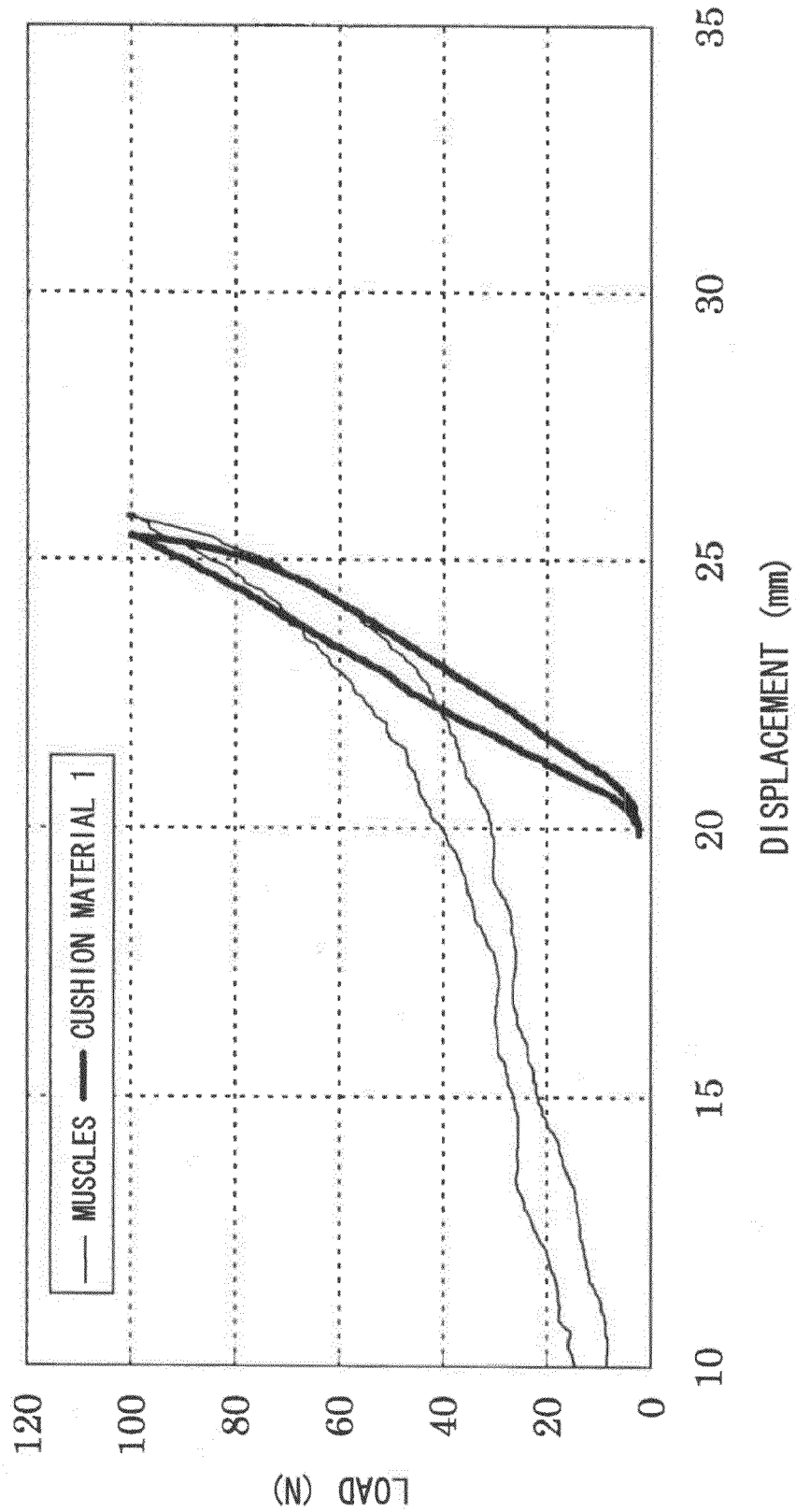
FIG. 4 is a graph showing a load-displacement characteristic of the air cushion shown in FIG. 3.

Here, the air cushion 10 was placed on a measuring board formed of a rigid flat plate and was pressed with a pressure board having a diameter of 98 mm in a thickness direction designated by an arrow in FIG. 3, and thereby the load-displacement characteristic (spring characteristic) thereof was measured and compared with the load-displacement characteristic (spring characteristic) of human muscles. The load-displacement characteristic of human muscles was obtained by pressing arm muscles with the pressure board having a diameter of 98 mm. The pressure occurring in the lumbar region or buttocks of a person seated in an equilibrium state ranges from 60 N to 80 N. In this pressure range, it can be seen from FIG. 4 that the load-displacement characteristic of the air cushion 10 approximates to the load-displacement characteristic of human muscles. Therefore, the air cushion 10 has the same characteristic as human muscles in terms of load-displacement characteristic (spring characteristic) when a pressure ranging from 60 N to 80 N is applied, and is appropriate for capturing bio-signals occurring through muscles.

The air cushions 10, 10 are disposed, as described above, in the portion supporting the lumbar region in the seat 100 for automobile. Specifically, the respective inside lower ends 10a, 10a of the air cushions 10, 10 were set to positions at 40 mm leftward and rightward respectively from the center of the seat back 110, and at 40 mm upward along the seat back 10 from the boundary between the seat cushion 120 and the seat back 110. The respective inside upper ends 10b, 10b of the air cushions 10, 10 were set to positions at 80 mm leftward and rightward respectively from the center of the seat back 110. When a Japanese male subject 167 cm tall, weighing 74 kg, and aged 31 sat on the seat 100, the air cushions 10, 10 were located approximately along the respective left and right iliocostalis lumborum muscles of the subject, and the respective upper ends of the air cushions 10, 10 were set at the height corresponding to the intermediate positions of the lower face and the upper face of the diaphragm of the subject.

Figure 5:
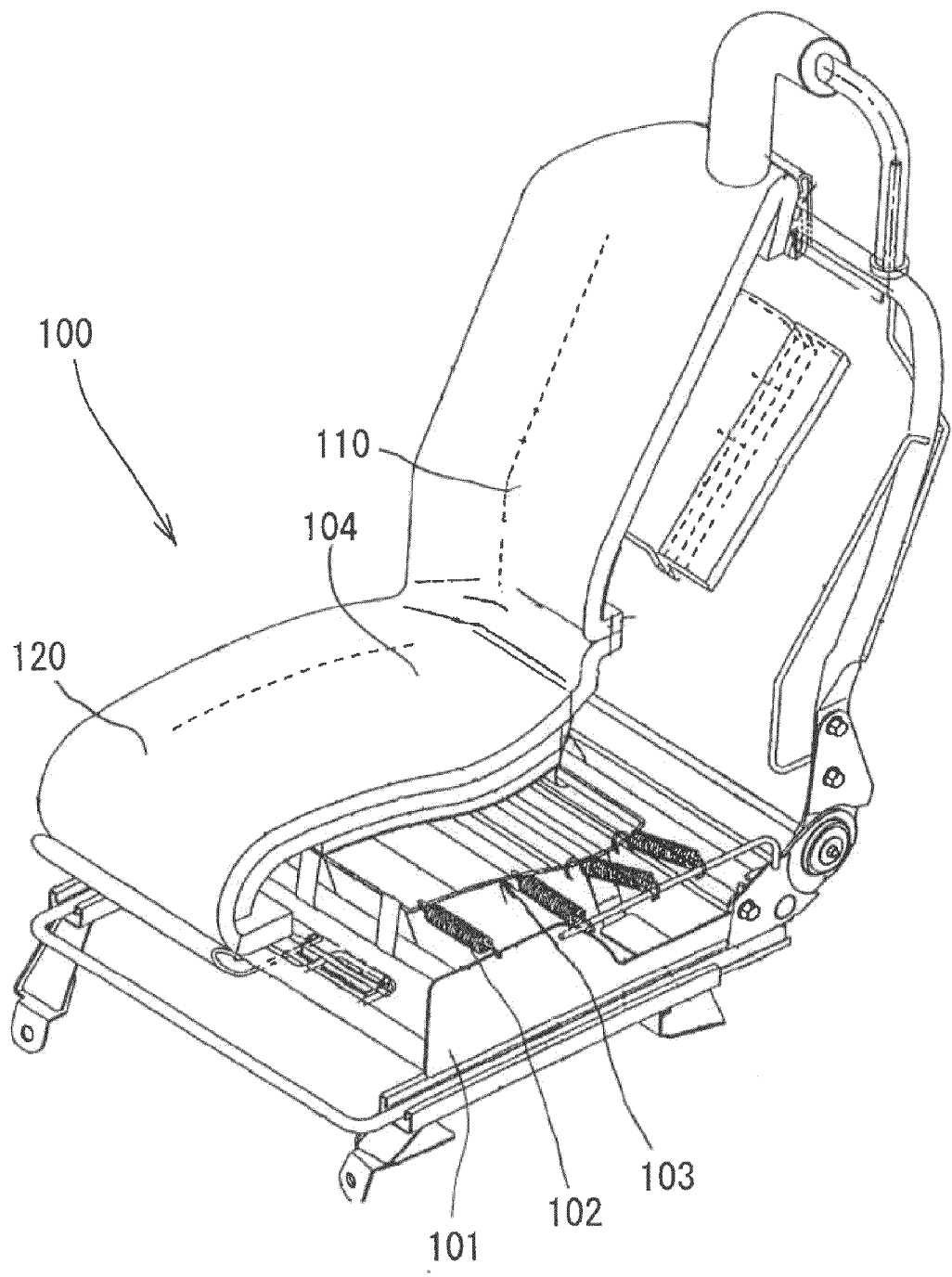
FIG. 5 is a view showing an example of a specific structure of a seat according to the embodiment.

The seat 100 includes, as shown in FIG. 5 for example, a flat support member 103 provided on the cushion frame 101 via coil springs 102 and a torsion bar (not shown), and a three-dimensional solid knitted fabric 104 stretched with a low tension covering the flat support member 103, and so on. By the operations of metal springs such as the coil springs 102 and the torsion bar, vibration with low frequency and large amplitude is absorbed, and by the tension of the three-dimensional solid knitted fabric 104 itself, vibration with high frequency and small amplitude is absorbed. Particularly, the three-dimensional solid knitted fabric 104 has a structure suspended by a predetermined tension in any position of the seat back unit 110 and the seat cushion unit 120, and can efficiently absorb forward/backward vibration at 5 Hz to 8 Hz inputted to the seat back unit 110. Therefore, this seat 100 has a quite high ability to damp external vibration inputted as noise.

Figure 6:
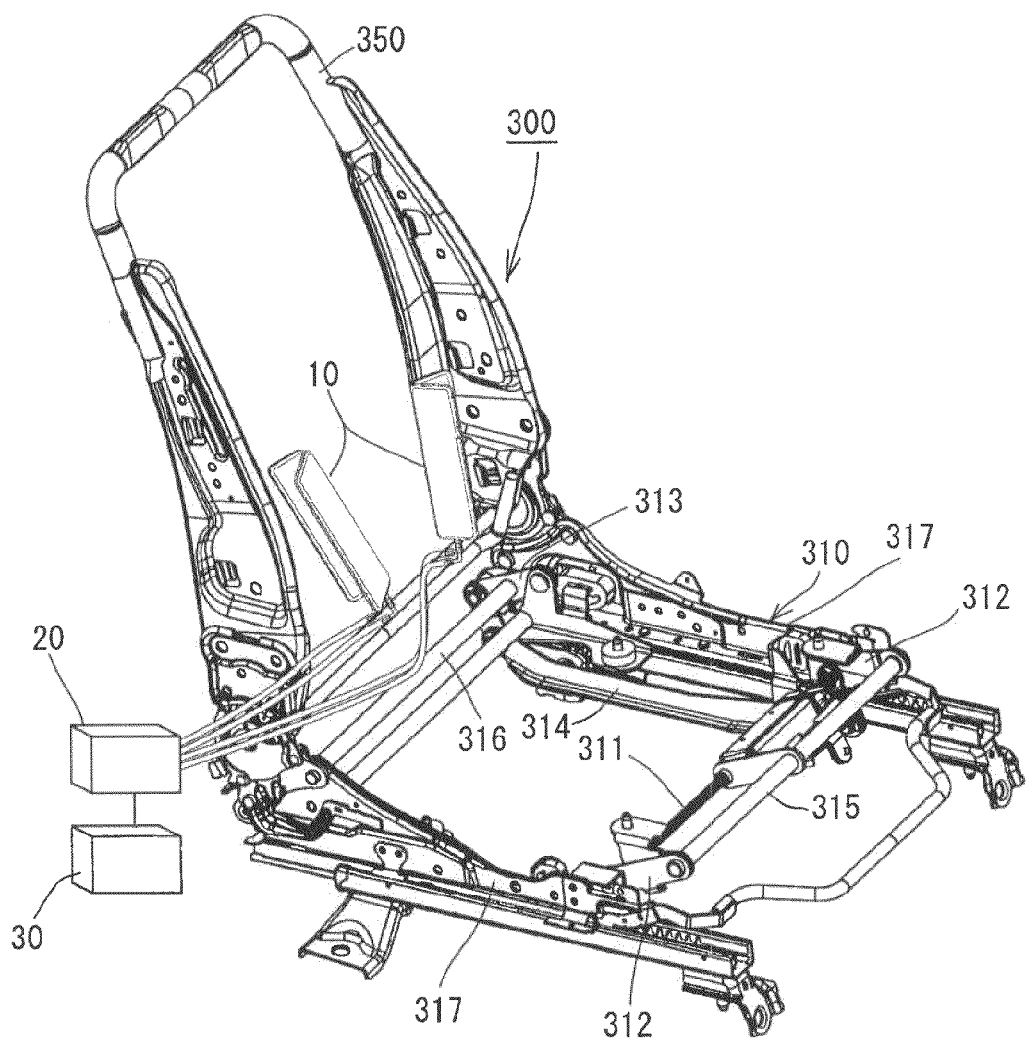
FIG. 6 is a view showing another example of a specific structure of a seat according to the embodiment.

Further, a seat 300 shown in FIG. 6 has a seat cushion unit 310 and a seat back unit 350, and the seat cushion unit 310 has side frames 317, 317. A torsion bar 311 is provided along a width direction in the vicinities of front ends of the side frames 317, 317. At end portions of the torsion bar 311, bent portion of first link plates 312, 312 formed in a substantially L shape are pivotally supported, and the torsion bar 311 is arranged to be twisted by displacement of the first link plates 112, 312 in a rotational direction. The first link plates 312, 312 in a substantially L shape each have a tip located more forward than the disposed position of the torsion bar 311, and a rear end provided in a direction to be located lower than the disposed position of the torsion bar 311. Between the tips of the first link plates 312, 312, a front end support frame 315 is provided transversely.

Further, in the vicinities of rear ends of the side frames 317, 317, there are provided second link plates 313, 313 formed in a substantially L shape with bent portions pivotally supported by the side frames 317, 317 respectively. Further, the second link plates 313, 313 in a substantially L shape each have a tip located more forward than the pivotal support positions of the bent portions, and a read end provided in a direction to be located lower than the pivotal support positions of the bent portions. Connection link plates 314 are provided respectively across the rear ends of the second link plates 313, 313 and the rear ends of the above-described first link plates 312, 312, where the first link plates 312, 312, the second link plates 313, 313 and the connection link plates 314 form a parallel link mechanism.

In this seat 300, since it has the above structure, the operating directions of the first link plates 312, 312 and the second link plates 313, 313 substantially match in upward and downward directions along the surface of the seat back 350. Therefore, when the human body vibrates in an upward direction by input of external vibration, the cushion material of the seat back 350 moves upward and obliquely rearward together with the human body. When the human body moves in a downward direction, the cushion material moves in a direction to push the buttocks forward while moving downward together with the human body. At the same time, the cushion material of the seat cushion unit 310 moves in forward and backward directions along with such input of external vibration. Consequently, due to the support by the parallel link mechanism pivotally supported directly by the torsion bar 312, the cushion material of the seat back unit 350 and the cushion material of the seat cushion unit 310 perform rotation movement following the movement of the human body caused by the input of external vibration. Thus, there is small relative movement of the human body and the cushion material, which lowers the resonance peak, thereby allowing improvement of the vibration absorbing characteristic. Further, due to the high following ability relative to movement of the human body, the influence of the input of external vibration becomes small, and the air pressure variation by a bio-signal can be detected sensitively when the air cushions 10 are arranged.

Here, input of upward and downward vibration by which a person feels unpleasant is roughly divided in two vibration modes. A shaky feeling that the body is shaken largely and a quivering feeling due to resonance of internal organs, which occur in the vicinities of 5 Hz and 8 Hz respectively. Particularly, there is a characteristic in motion of the lumbar region. The vibration that occurs in the vicinity of 5 Hz causes bending of the entire spine like rotational movement in forward and backward directions about and below the chest, while the upper body of the person barely moves. The vibration in the vicinity of 8 Hz causes the spine to move upward and downward with the buttocks play a role as a spring. However, bending of the lumbar vertebral region occurring at the same time suppresses movement of the upper body. Further, when the masses of the head and chest are applied to the upper portion of the spine, movement of the spine upper portion is further restricted. The larger the balance of head mass of a person, the smaller the influence of the back of a seat becomes. The smaller the sizes of the body and head of a person, the more sensitive this person is to back slapping from the back of a seat. Accordingly, for suppressing vibration transmitted to a human body, it is preferable that the cushion material of the three-dimensional solid knitted fabric or the like provided in the seat back part and the seat cushion part is provided to follow well the motion of a person corresponding to input of such vibration. Further, with such a structure, in particular the structure shown in FIG. 6 described above, the air cushion 10 arranged corresponding to the portion supporting the lumbar region follows the motion of a person well, together with the cushion material. Incidentally, it is preferable that the cushion material of the seat back part is supported to be movable upward and downward by engaging the cushion material slidably with the frame materials arranged in an upward and downward direction, and supporting at least one of the upper portion and the lower portion of the three-dimensional solid knitted fabric on the back frame via coil springs.

Figure 7:
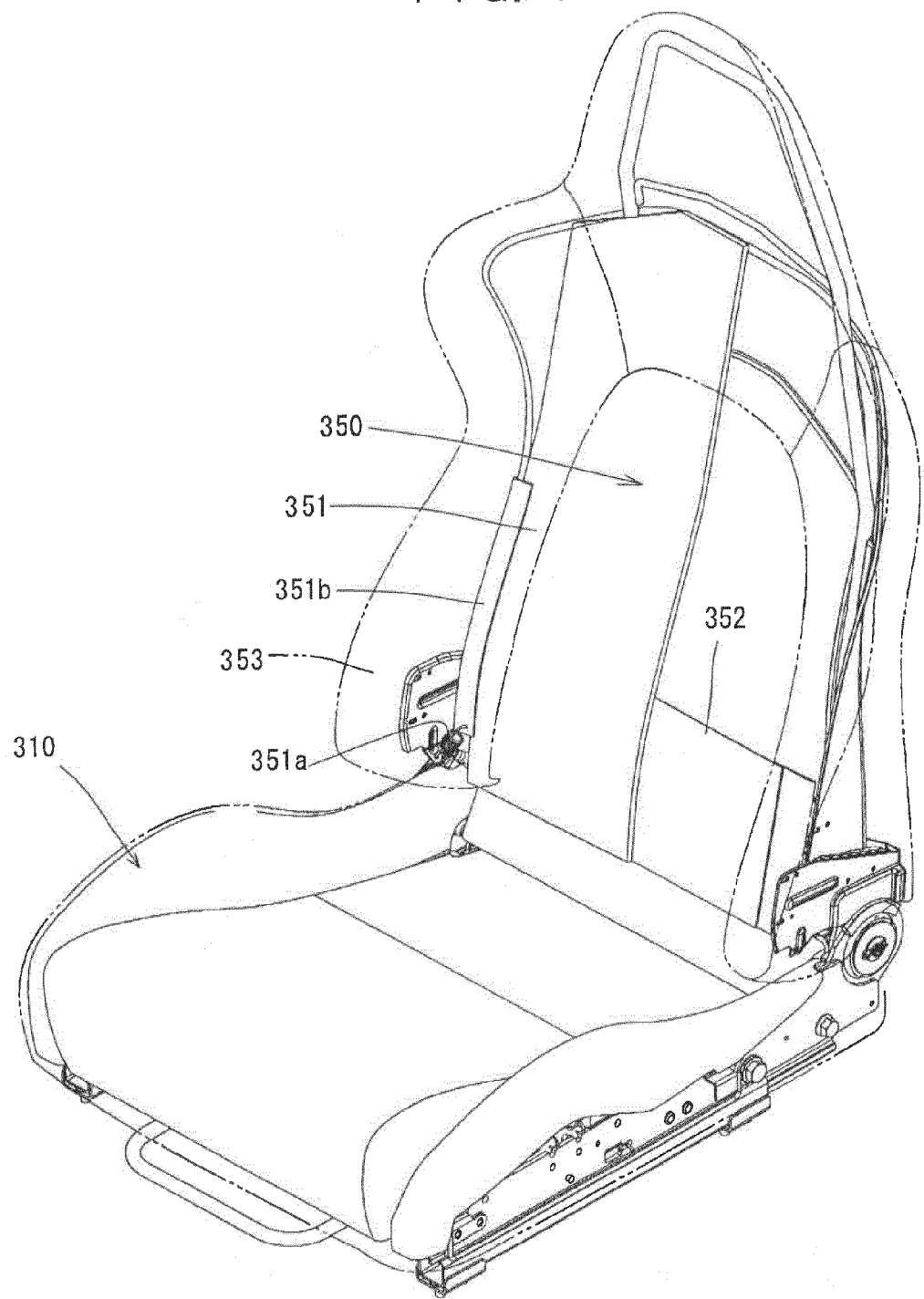
FIG. 7 is a view showing a main part of a more preferable structure of the seat used in FIG. 6.

FIG. 7 shows an example of this, showing a structure in which the seat back part 350 includes a cushion material 353 on a surface layer, a base cushion material 351 disposed on a back face side thereof, and a cushion material 352 for supporting pelvis disposed further on a back face side thereof. Among them, the base cushion material 351 has a lower end edge supported by a coil spring 351a coupled to a frame disposed in the vicinity of a rear portion of the seat cushion part 310, and a resin member 351b for engagement having a low friction coefficient is attached to a side edge thereof. This resin member 351b for engagement is engaged with a frame member disposed along the upward and downward direction in the vicinity of the side edge of the seat back part 150, and thereby the base cushion material 351 has a structure capable of vibrating vertically. The cushion material 352 for supporting pelvis is strained along the width direction between side frames of the seat back part 350, and has a structure to support the vicinity of the pelvis while slightly pressing the pelvis. This facilitates, when external vibration is input, movement of the cushion material of the seat back part 350, particularly the base cushion material 351, in upward and downward directions along the torso line while seated, following the behavior of the human body when vibrating, thereby reducing relative movement of the human body and the cushion material.

Figure 8:
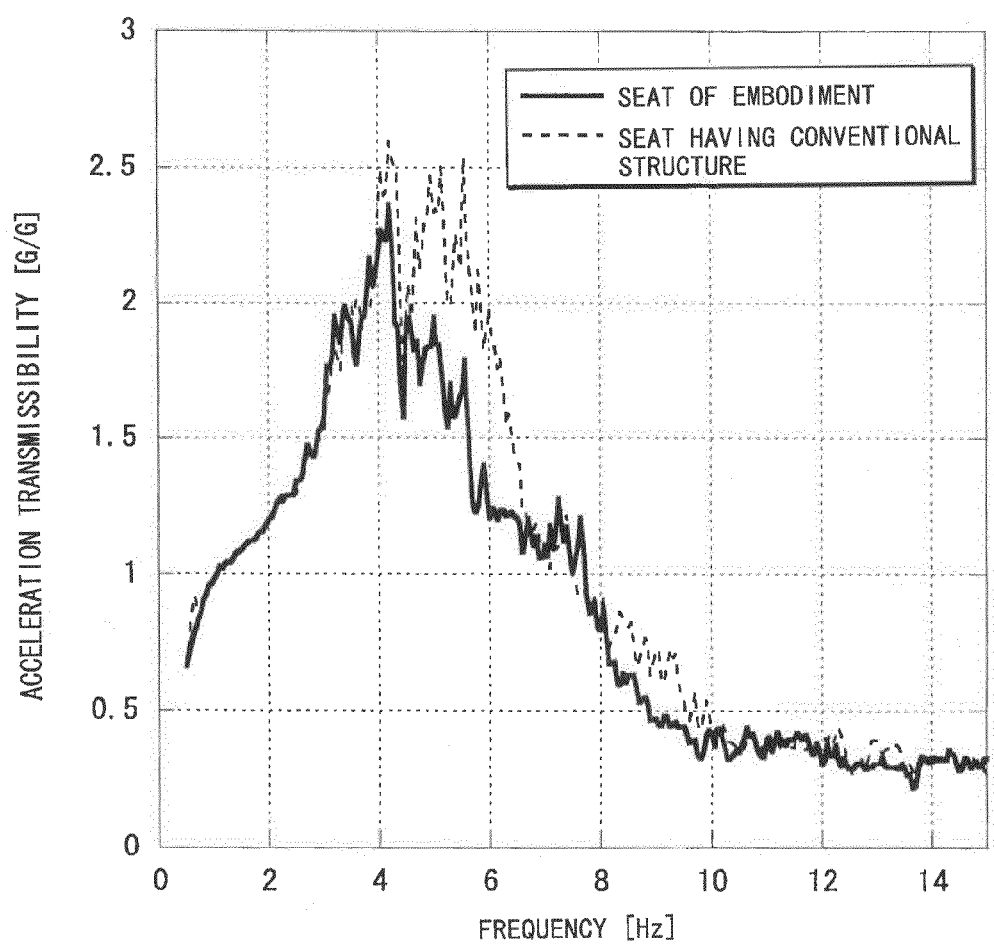
FIG. 8 is a graph showing acceleration transmissibilities when vibration is applied with random waves to the seat in FIG. 6 and a seat having a conventional structure.
Figure 9A:
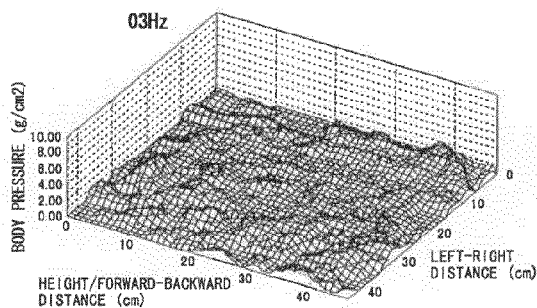
FIGS. 9A to 9H are graphs showing body pressure distributions in a seat back part of the seat in FIG. 6 with respect to frequencies from 3 Hz to 10 Hz.
Figure 9E:
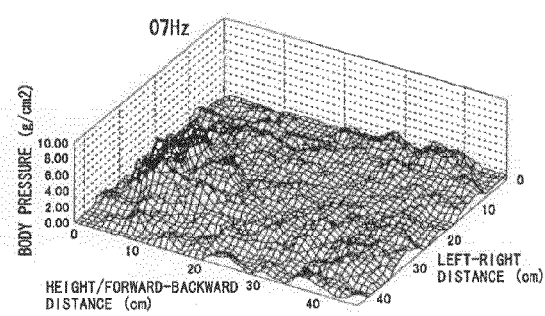
Figure 9B:
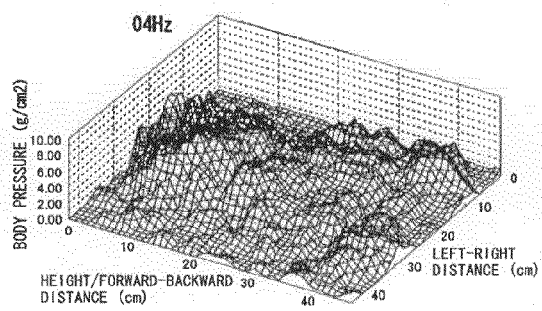
Figure 9F:
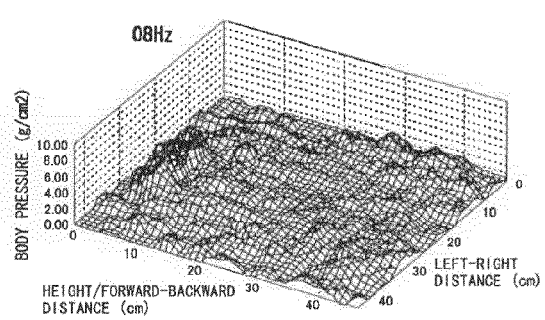
Figure 9C:
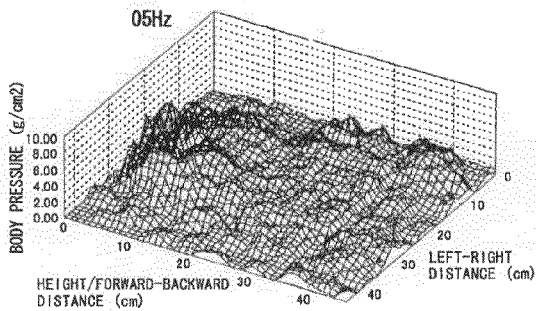
Figure 9G:
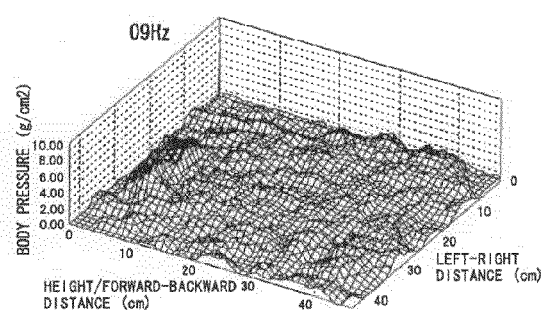
Figure 9D:
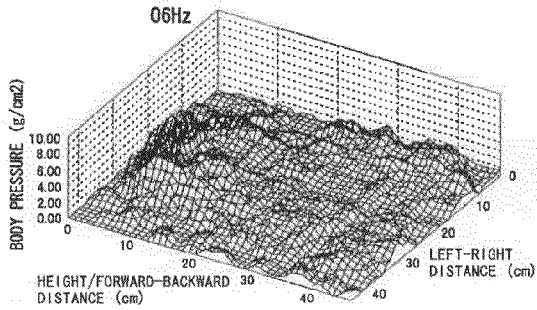
Figure 9H:
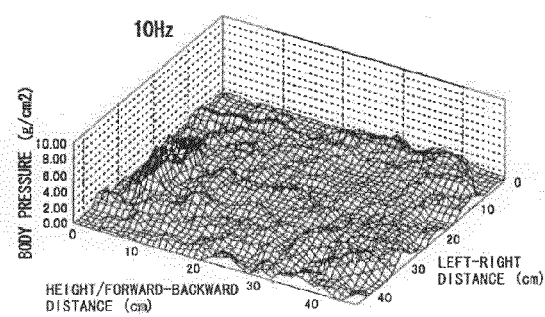

Incidentally, the structures shown in FIG. 5 to FIG. 7 are merely examples. However, such structures are preferable for detecting a bio-signal because an air pressure variation due to a bio-signal can be detected sensitively when the air cushions 10 are arranged in the seat 300 shown in FIG. 6 and FIG. 7. To verify this point, a vibration experiment was conducted such that the seat 300 is attached to a platform of a vibrator, an acceleration sensor is attached in the vicinity corresponding to positions below the ischial tuberosities in the seat cushion, a Japanese male weighing 68 kg is seated on each vehicle seat, and vibration is applied thereto with random waves. In addition, for comparison, the same experiment was conducted with a seat having a conventional structure which does not have the parallel link mechanism and in which a urethane material is arranged on a cushion pan. FIG. 8 shows acceleration transmissibility (G/G) when vibration is applied with random waves. FIGS. 9A to 9H are graphs showing body pressure distributions in the seat back part of the seat 300 having the parallel link mechanism when random vibration was performed, with respect to frequencies from 3 Hz to 10 Hz. FIGS. 10A to 10H are graphs showing body pressure distributions in a seat back part when the same test was performed while seated on the seat having the conventional structure formed by supporting a urethane material on a cushion pan, similarly with respect to frequencies from 3 Hz to 10 Hz.

As is clear from FIG. 8, the seat 300 has a lower resonance point than that of the seat having the conventional structure, and it can be seen that the vibration absorption characteristic in a high frequency band of 8 Hz and higher is largely improved. Further, normally, when the spring constant gets softer, the resonance point shifts to a low frequency but the gain increases. However, the seat 300 has the structure with a high follow-up ability to motion of a person accompanying input of vibration, due to an upward and downward movement mechanism of the parallel link mechanism and the cushion material of the seat back part 350 described above. Accordingly, with respect to motion of a person along the surface of the seat back part 350 due to the parallel link mechanism, when the cushion material forming the seat back part 350 is the three-dimensional solid knitted fabric, relative displacement of the three-dimensional solid knitted fabric and the person becomes small due to friction, viscosity, and elasticity, resulting in a skyhook effect which is felt like parrying. Further, in the vicinity from the pelvis to the lumbar part of a person, friction force by the pressure bearing capacity of the cushion material 352 for supporting pelvis shown in FIG. 7 increases. Thus, at the resonance point, a resonance point passing phenomenon occurs such that an opposite phase occurs relative to input of vibration in a vertical direction and the gain decreases, and the vibration absorption characteristic is improved by integral motion of the human body and the cushion material. Further, when a urethane material or any other spring structure is adopted, instead of the three-dimensional solid knitted fabric, for the seat back part 350 of the seat 300 adopting the parallel link structure, there occurs so to speak a forceful sky-hook effect by force using collision vibration, resulting in improvement of vibration characteristic around the resonance point.

Further, in the seat having the conventional structure, input of external vibration operates to disturb respiratory movement, but in this embodiment the support pressure to the lumbar vertebral region is increased so as to facilitate abdominal breathing. That is, the lumbar support is not high in a static state, but when vibration is inputted due to traveling, motion of the parallel link mechanism presses the lumbar vertebral region against the seat back part 350. Since the cushion material 352 for supporting pelvis shown in FIG. 7 is disposed for the lumbar vertebral region, pressing against the seat back part 350 by the parallel link mechanism causes increase in support pressure to a region where continuous feeling is missing on the vertical cross section corresponding to the input vibration, to thereby eliminate a part where a prominent surface pressure exists. Also, movement of the thoracic vertebra region is small, and a fluctuation occurs at the lumbar part, thereby helping respiratory movement. Comparing FIG. 9 with FIG. 10 in this respect, in the seat 300 shown in FIG. 9 the pressure of a pelvis upper edge increases by any frequency of the external vibration inputted, and this becomes a support for the pelvis upper edge. It can be seen that the aforementioned pressure to the region where continuous feeling is missing on the vertical cross section is increased. Particularly, seeing data from 7 Hz to 10 Hz, the pressure in the chest region is small, pressure variation concentrates at the pelvis, and motion of the pelvis is not hindered, resulting in motion facilitating respiratory movement. In contrast, in the seat having the conventional structure in FIG. 10, the pressure in the vicinity of the pelvis upper edge is low, which provides no support for the pelvis upper edge. The increase of the support pressure of the lumbar vertebrae corresponding to input vibration leads to that, when the air cushions 10 are disposed as shown in FIG. 6 disposed at the positions corresponding to the lumbar vertebral region, the contact between the air cushions 10 and the human body increases, and the pressure variation in the chest region becomes small. Thus, the bio-signal detecting sensitivity improves.

In the following test example, the seat 300 shown in FIG. 6 and FIG. 7 was attached in the driver's seat area of a compact car, and tests were carried out.

Test Example 1

Seventeen healthy Japanese males and three healthy Japanese females aged in their twenties to thirties were selected as subjects. They were each seated on the seat 300 for five minutes in a resting state with the vehicle being in a static state, and human conditions in this period were checked. In test example 1, outputs due to air pressure variations of the air cushions 10 obtained by the analyzing means 30 from the air pressure measuring instrument 20 were filtered through an analog signal processing circuit so as to separate them into breath components and heartbeat components, and respective spectral waveforms of the heartbeat components and the breath components were obtained. Incidentally, in the filtering process, fourth-order filtering is performed in bands of 0.1 Hz to 0.5 Hz and 0.5 Hz to 2.0 Hz, to thereby separate the breath components and the heartbeat components. The sampling frequency is 200 Hz and the resolution is 12 bit.

Further, to obtain correlativity with bio-signals obtained from the air cushions 10, an optical finger tip pulse wave meter was attached to the left index finger of each subject to measure finger tip volume pulse waves, and a distortion type respirometer was attached to the chest region of each subject to measure breathing. The measured data were processed, and spectral waveforms of heartbeats were obtained from the finger tip volume pulse wave meter and spectral waveforms of breaths were obtained from the distortion type respirometer.

Figure 11A:
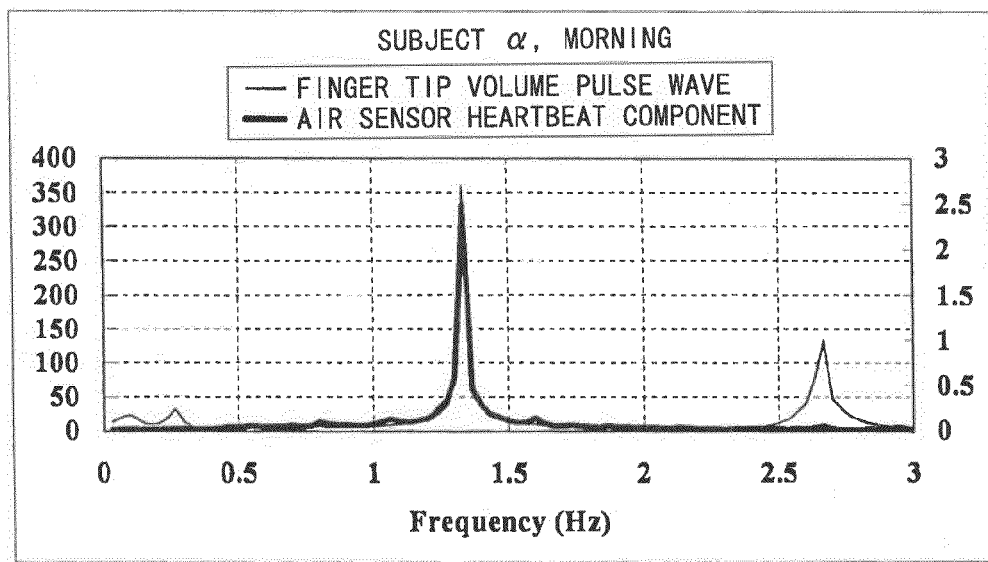
FIG. 11A shows a spectral waveform of heartbeat components obtained from finger tip volume pulse waves and a spectral waveform of heartbeat components obtained from air cushions.
Figure 11B:
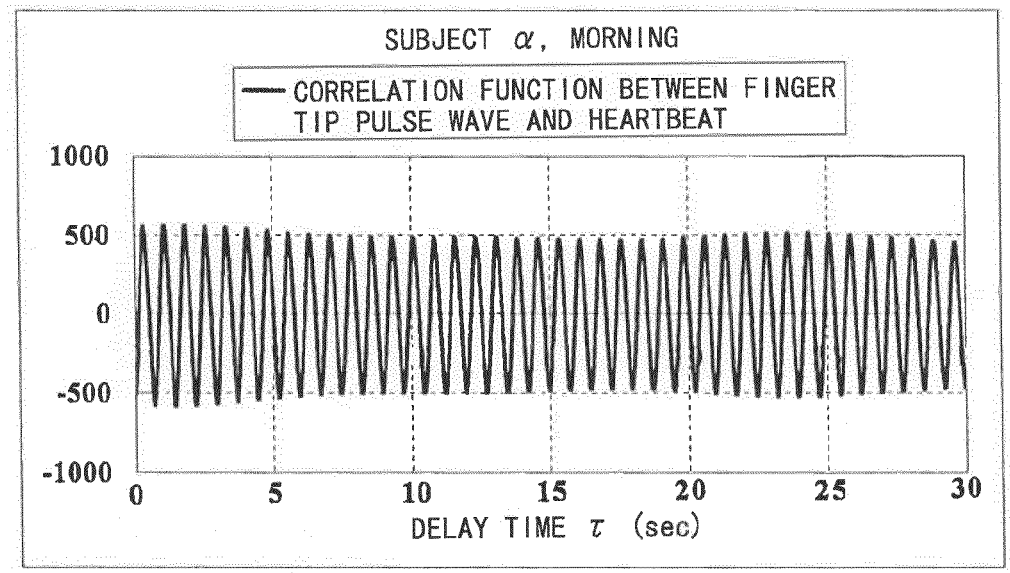
FIG. 11B shows a correlation function of them.

FIG. 11A shows the spectral waveform of the heartbeat components obtained from the finger tip volume pulse waves and the spectral waveform of the heartbeat components obtained from the air cushions 10. FIG. 11B is a graph showing the correlation function of them. FIG. 12A shows the spectral waveform of the breath components obtained from the distortion type respirometer and the spectral waveform of the breath components obtained from the air cushions 10. FIG. 12B is a graph showing the correlation function of them.

As is clear from these graphs, peaks of the heartbeat components were obtained at 1.3 Hz from both the finger tip volume pulse waves and the air cushions 10, and peaks of the breath components were obtained at 0.27 Hz from both the distortion type respirometer and the air cushions 10. In comparison of the 20 subjects, there are differences in correlativity but the peak frequencies of all the subjects matched. On the other hand, regarding cross correlation functions, 13 heartbeat components were obtained in ten seconds, and three breath components were obtained in ten seconds, which matched the respective spectra. From the above, in a static seating state, it can be seen that it is possible to sense heartbeat components and breath components by the bio-signal analyzer 1 including the air cushions 10 according to the above embodiment, in both the aspects of frequency axis and time axis.

Test Example 2

Figure 13A:
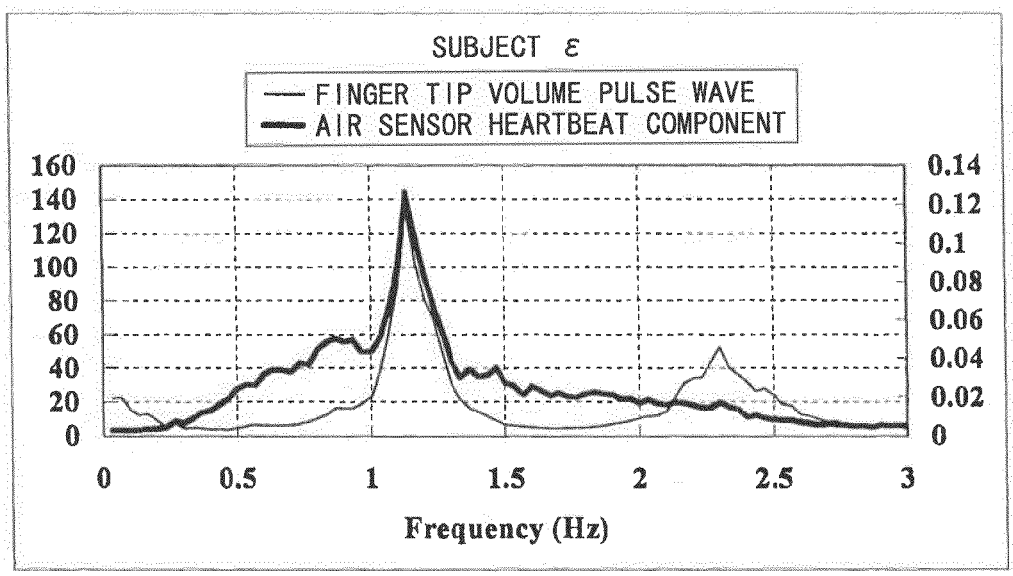
FIG. 13A shows a spectral waveform of heartbeat components obtained from finger tip volume pulse waves and a spectral waveform of heartbeat components obtained from air cushions.
Figure 13B:
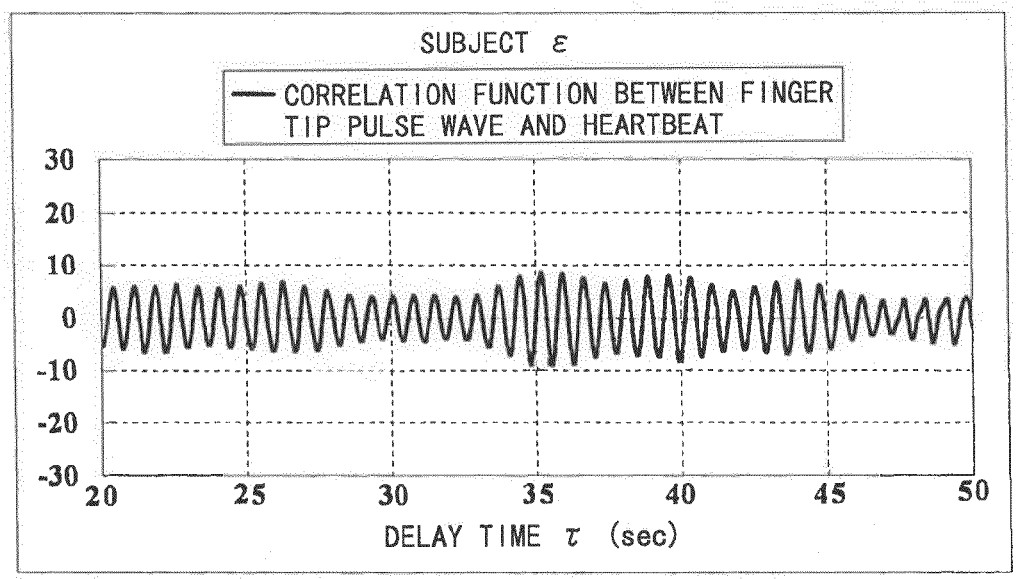
FIG. 13B shows a correlation function of them.
Figure 14A:
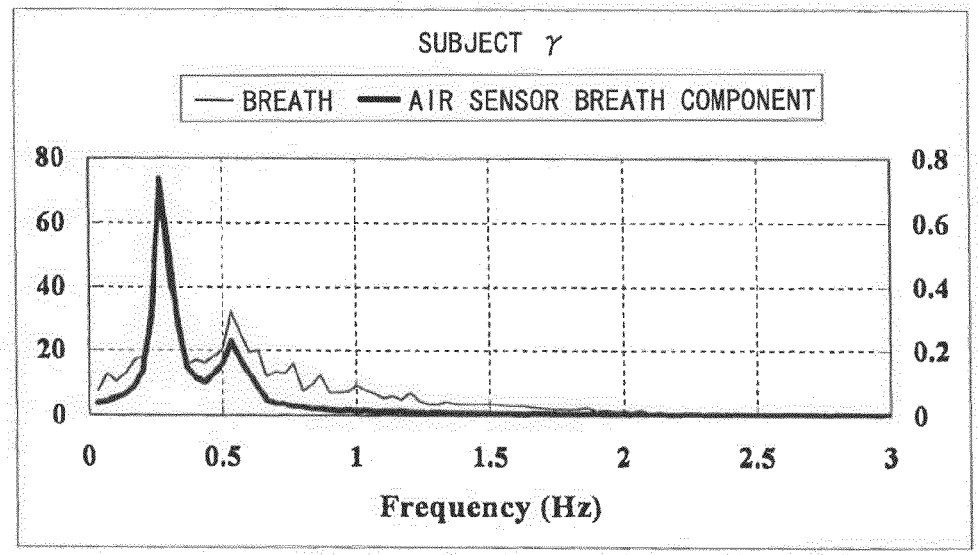
FIG. 14A shows a spectral waveform of breath components obtained from a distortion type respirometer and a spectral waveform of breath components obtained from the air cushions 10.
Figure 14B:
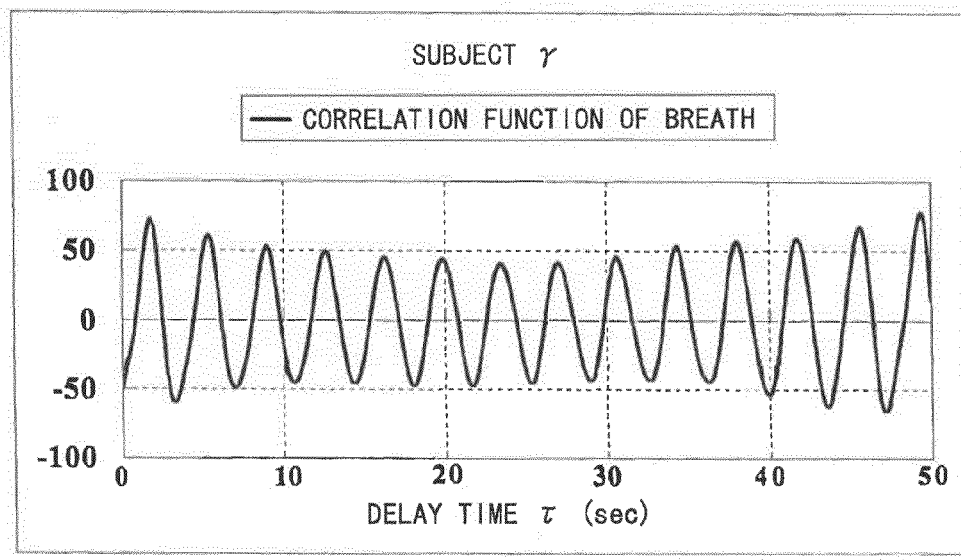
FIG. 14B shows a correlation function of them.

The same test as the test example 1 was carried out on eight subjects out of the 20 subjects in the test example 1 in an idling state of an actual vehicle. Results are shown in FIG. 13 and FIG. 14. FIG. 13A shows a spectral waveform of heartbeat components obtained from finger tip volume pulse waves and a spectral waveform of heartbeat components obtained from the air cushions 10, and FIG. 13B is a graph showing the correlation function of them. FIG. 14A shows a spectral waveform of breath components obtained from the distortion type respirometer and a spectral waveform of breath components obtained from the air cushions 10, and FIG. 14B is a graph showing the correlation function of them.

Peaks of the heartbeat components were obtained at 1.3 Hz from both the finger tip volume pulse waves and the air cushions 10, and peaks of the breath components were obtained at 0.25 Hz from both the distortion type respirometer and the air cushions 10. Regarding cross correlation functions, 13 heartbeat components were obtained in ten seconds, and three breath components were obtained in ten seconds, which matched the respective spectra. In this idling state, heartbeat components were detected from all the eight subjects, and breath components were detected from six out of the eight subjects. Therefore, it was made clear that, also in an idling state, it is possible to sense heartbeat components and breath components by the bio-signal analyzer 1.

Test Example 3

Figure 15A:
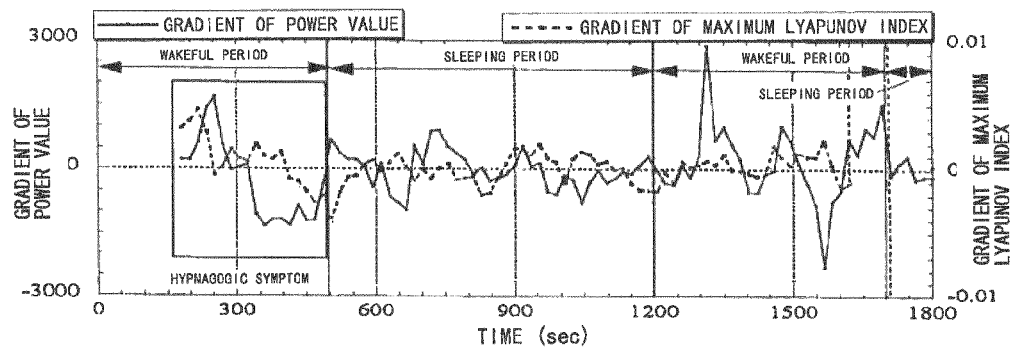
FIG. 15A shows time-series waveforms of respective gradients of power values and maximum Lyapunov indexes related to the breath components obtained from the air cushions.
Figure 15B:
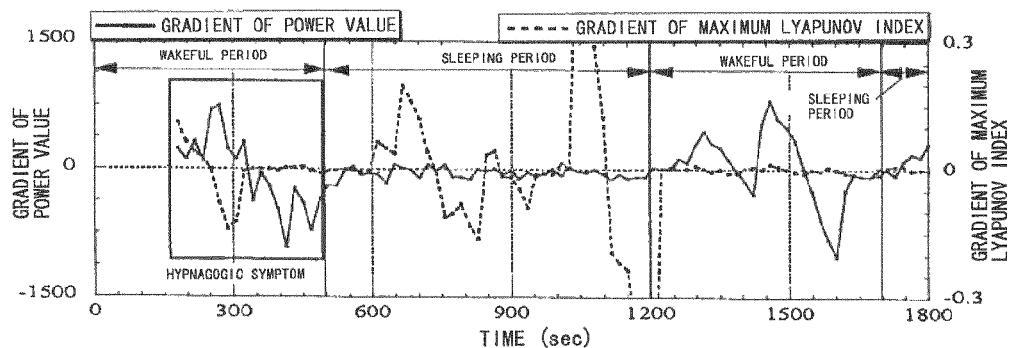
FIG. 15B shows time-series waveforms of respective gradients of power values and maximum Lyapunov indexes related to the heartbeat components obtained from the air cushions.
Figure 15C:
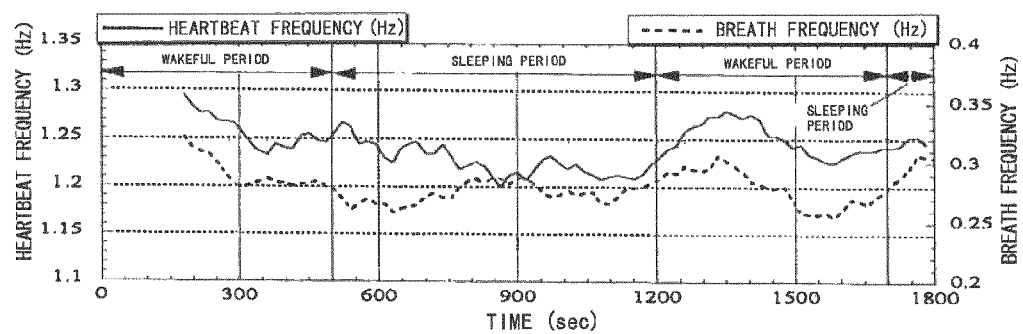
FIG. 15C shows time-series waveforms of frequencies of the heartbeat components and the breath components obtained from the air cushions.

Three healthy Japanese male subjects in their twenties to thirties were seated, each subject was further instructed to close eyes and sleep after being seated, and a sleep experiment was performed in a resting posture for 30 minutes. Air pressure variations sampled by the air cushions 10 of the bio-signal analyzer 1 of the above embodiment were, similarly to the test example 1 an the test example 2, filtered through the analog signal processing circuit by the analyzing means 30, and thereafter separated into breaths components and heartbeat components. Then time series signals of the heartbeat components and the breath components were used to create a time-series waveform of a gradient of power values and a time-series waveform of a gradient of maximum Lyapunov indexes, respectively, and it was studied whether or not there appears a waveform representing a hypnagogic symptom. FIG. 15 to FIG. 17 which will be described below each show test results of one of the three subjects. FIG. 15A shows time-series waveforms of respective gradients of power values and maximum Lyapunov indexes related to the breath components obtained from the air cushions 10, and FIG. 15B shows time-series waveforms of respective gradients of power values and maximum Lyapunov indexes related to the heartbeat components obtained from the air cushions 10. Further, FIG. 15C shows time-series waveforms of frequencies of the heartbeat components and the breath components obtained from the air cushions 10.

Incidentally, calculation of the time-series waveform of the gradient of the power values and the time-series waveform of the gradient of the maximum Lyapunov indexes uses a method proposed by the present applicants in Japanese Patent Application Laid-open No. 2004-344612. Specifically, for the respective time-series signals of the heartbeat components and the breath components which are detected and separated, maximum values and minimum values are obtained by smoothing differentiation by Savitzky and Golay. Then, the maximum values and minimum values are divided by every five seconds and an average value is obtained from each of them. The square of the difference between the respective average values of the obtained maximum values and minimum values is taken as a power value, and this power value is plotted every five seconds to make a time-series waveform of the power values. The gradient of power values is obtained by least square method for a certain time width Tw (180 seconds), so as to read a global change of the power values from this time-series waveform. Then, for the next time width Tw, similar calculation is performed for an overlap time T1 (162 seconds) and results are plotted. One obtained by sequentially repeating this calculation (slide calculation) becomes the time-series waveform of the gradient of the power values. The time-series waveform of the gradient of the maximum Lyapunov indexes is is obtained similarly by chaos analyzing the respective time-series signals of the heartbeat components and the breath components which are detected and separated so as to calculate the maximum Lyapunov indexes, and thereafter obtaining maximum values and minimum values by smoothing differentiation similarly to the above and slide calculation of them.

Figure 16A:
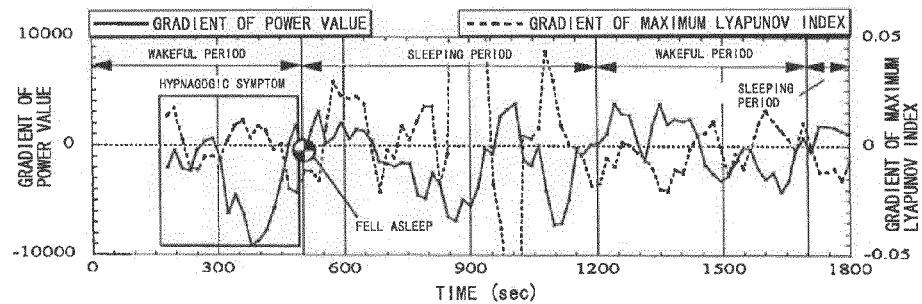
FIG. 16A is a graph showing time-series waveforms of respective gradients of power values and maximum Lyapunov indexes of the finger tip volume pulse waves.

For verification, a finger tip volume pulse wave meter and a simplified electroencephalograph were attached to each subject, and finger tip volume pulse waves and brain waves were measured. FIG. 16A shows time-series waveforms of respective gradients of power values and maximum Lyapunov indexes of the finger tip volume pulse waves, and FIG. 16B shows time-series changes of distribution ratios of θ wave, α wave, and β wave of brain waves.

Now, as reported in WO2005/092193 by the present applicants, on the time-series waveform of the power value gradient of the finger tip volume pulse waves, a waveform with large amplitude appears at low frequency, and preferably, at this time, a time point when the power value gradient and the maximum Lyapunov index gradient stably exhibit a phase difference of substantially 180 degrees in the time-series signal can be judged as a hypnagogic symptom signal. In the time-series waveforms of FIG. 16A, the waveform showing this hypnagogic symptom appears in the vicinity of 150 seconds to 500 seconds. Comparing this with the time-series waveforms of the respective gradients of the breath components and the heartbeat components obtained from the air cushions 10 of FIG. 15A, 15B, the power value gradient of the breath components or the heartbeat components obtained from the air cushions 10 in an almost same time zone as in FIG. 16A becomes a waveform with large amplitude at low frequency. Accordingly, it can be seen that a hypnagogic symptom can be captured using the air cushions 10 of the above embodiment. However, comparing FIG. 15A with FIG. 15B, in the case of this subject, it is easier to capture a hypnagogic symptom in the gradient time-series waveform of the heartbeat components obtained from the air cushions 10 than in that of the breath components thereof.

Figure 16B:
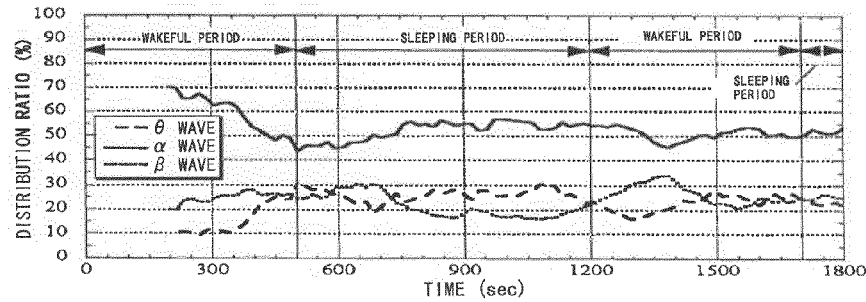
FIG. 16B is a graph showing time-series changes of distribution ratios of θ wave, α wave, and β wave of brain waves.

Studying a hypnagogic state and a wakeful state with the distribution ratios of brain waves shown in FIG. 16B, the moment to enter sleep is when the distribution ratio of α wave goes under 50% and the distribution ratio of θ wave starts to increase rapidly. Accordingly, it is proved that this subject fell asleep at 500 seconds after the start of experiment, awaked in the middle at 1200 seconds after the start, and fell asleep again at 1700 seconds after the start.

Figure 17A:
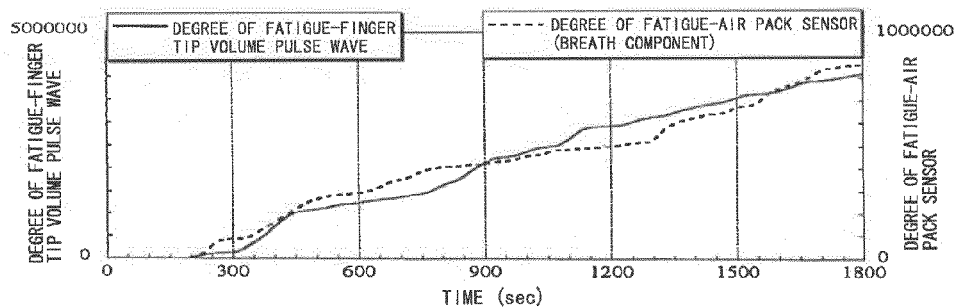
FIG. 17A is a graph showing comparison of the degree of fatigue obtained from time-series waveforms of gradients of breath components obtained from the air cushions with the degree of fatigue obtained from gradient time-series waveforms of finger tip volume pulse waves.
Figure 17B:
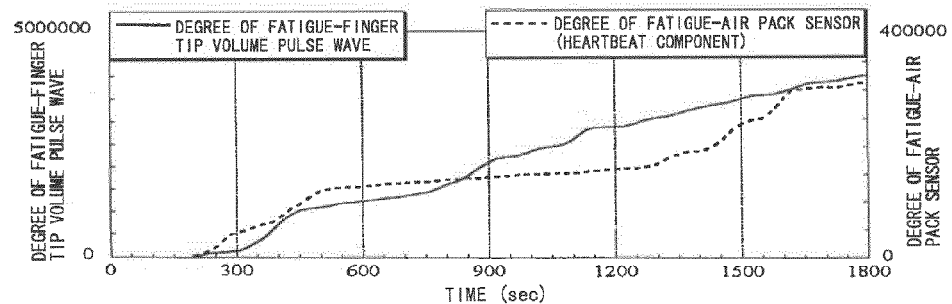
FIG. 17B is a graph showing comparison of the degree of fatigue obtained from time-series waveforms of gradients of heartbeat components obtained from the air cushions with the degree of fatigue obtained from gradient time-series waveforms of finger tip volume pulse waves.

Next, the respective degrees of fatigue obtained from the time-series waveforms of the respective gradients of heartbeat components and breath components obtained from the air cushions 10 are compared with the respective degrees of fatigue obtained from the gradient time-series waveform of the finger tip volume pulse waves of FIG. 16A and shown in FIG. 17A, 17B. Consequently, in the case of this subject, the degree of fatigue calculated from the breath components obtained from the air cushions 10 matched better in tendency with the degree of fatigue calculated from the finger tip volume pulse waves than the degree of fatigue calculated from the heartbeat components. Therefore, it is desirable that judging of the fatigue of this subject is based on the degree of fatigue calculated from the breath components. When judging fatigue, which of breath components and heartbeat components should be used differs among individuals. Thus, when it is judged using, for example, the bio-signal analyzer 1 of the present invention incorporated in the seat 300 for automobile, it is preferable that an arrangement is made to allow initial setting of which of breath components and heartbeat components obtained from the air cushions 10 should be selected by comparing with the degree of fatigue obtained from the finger tip volume pulse waves in advance. Incidentally, although not shown, almost the same results as the above subject were obtained from the other two subjects.

Test Example 4

Figure 18A:
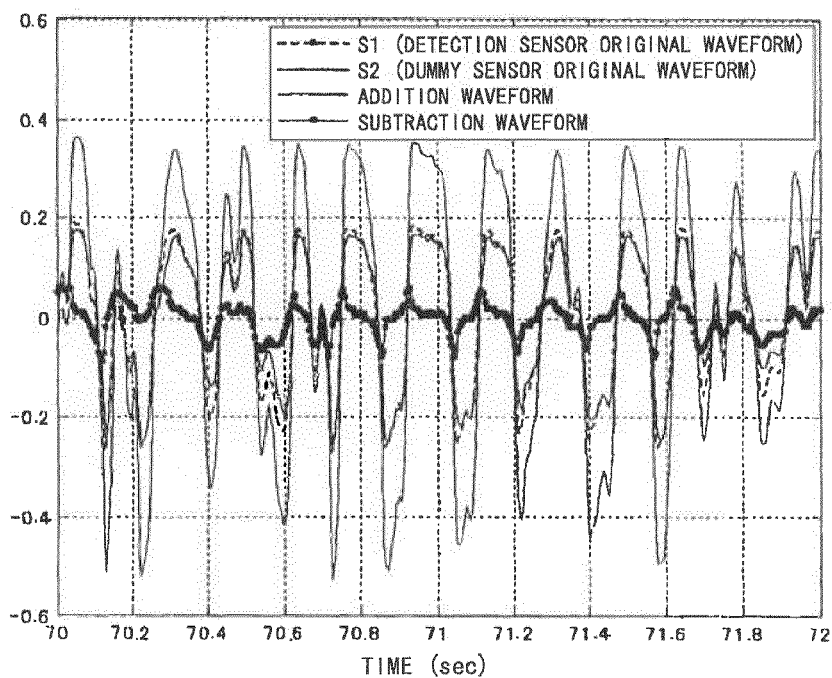
FIG. 18A shows original waveforms in time series of the air bags, original waveforms in time series when values of air pressure variations obtained from the air bags are added (addition waveform), and original waveforms in time series when the values are subtracted (subtraction waveform)
Figure 18B:
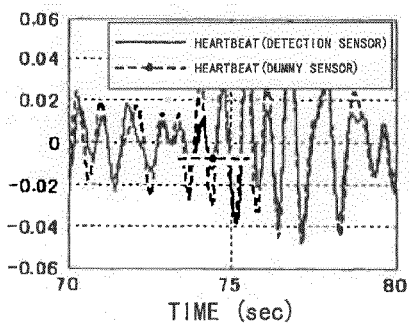
FIG. 18B shows time-series waveforms of the air bags with respect to heartbeat components separated by filtering processing.
Figure 18D:
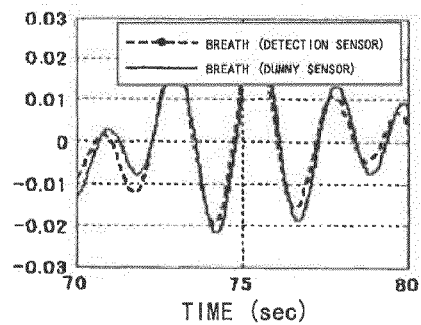
FIG. 18D shows time-series waveforms of the air bags with respect to breath components separated by filtering processing.
Figure 18C:
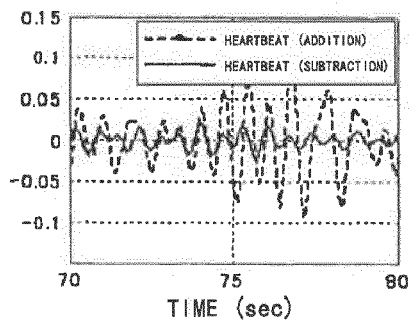
FIG. 18C is shows time-series waveforms when the time-series waveforms of heartbeat components of a detection sensor and a dummy sensor in FIG. 18B are addition processed and when they are subtraction processed.
Figure 18E:
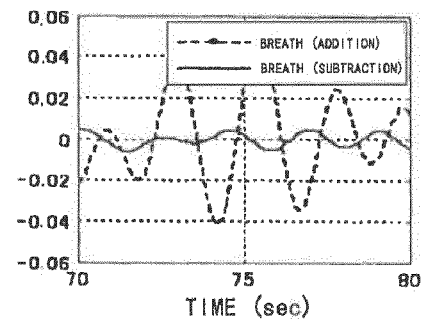
FIG. 18E shows time-series waveforms when the time-series waveforms of breath components of the detection sensor and the dummy sensor in FIG. 18D are addition processed and when they are subtraction processed.

Next, the effectiveness of bio-signal sampling was verified for when values of the air pressure variation of the air bags 11, 11 of the air cushions 10 are addition processed and when they are subtraction processed. In this test, a subject was tested while seated on the seat 300 of the above test example 1 in a resting state for a predetermined time. Results are shown in FIG. 18. FIG. 18A shows original waveforms in time series of the air bags 11, 11 (one arranged close to a human body is S1 (detection sensor), and the other is S2 (dummy sensor)), original waveforms in time series when values of air pressure variations obtained from the air bags 11, 11 are added (addition waveform), and original waveforms in time series when the values are subtracted (subtraction waveform). FIG. 18B shows time-series waveforms of the air bags 11, 11 (the detection sensor and the dummy sensor) with respect to heartbeat components separated by filtering processing. FIG. 18C shows time-series waveforms when the time-series waveforms of heartbeat components of the detection sensor and the dummy sensor of FIG. 18B are addition processed and when they are subtraction processed. FIG. 18D shows time-series waveforms of the air bags 11, 11 (the is detection sensor and the dummy sensor) with respect to breath components separated by filtering processing. FIG. 18E shows time-series waveforms when the time-series waveforms of breath components of the detection sensor and the dummy sensor in FIG. 18C are addition processed and when they are subtraction processed.

As is clear from these graphs, it can be seen that the addition processing allows to detect the air pressure variation accompanying a bio-signal more prominently than by the values of the individual air bags 11, 11 (the detection sensor and the dummy sensor). Particularly, under the situation that external vibration during traveling is inputted, the addition processing allows to prominently pick up values of a part where a bio-signal is obtained. On the other hand, the subtraction processing has a possibility to remove the influence of external vibration (noise), but in this test example, the influence of decreasing the amount of air pressure variation is larger in the subtraction processing. Thus, it was found that the addition processing is more effective.

Test Example 5

Figure 19A:
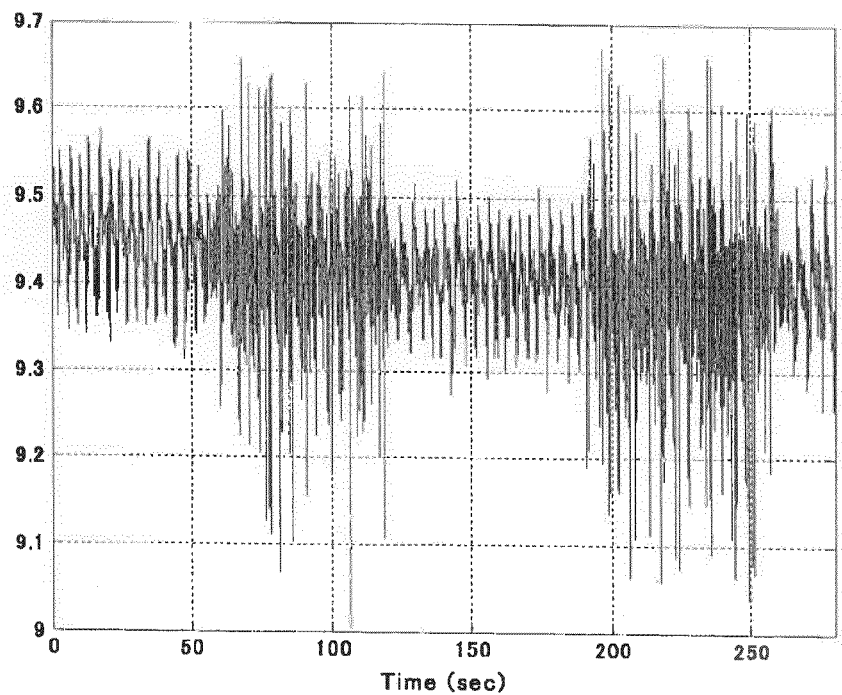
FIG. 19A shows a time-series original waveform of a voice signal obtained from the air cushions.
Figure 19B:
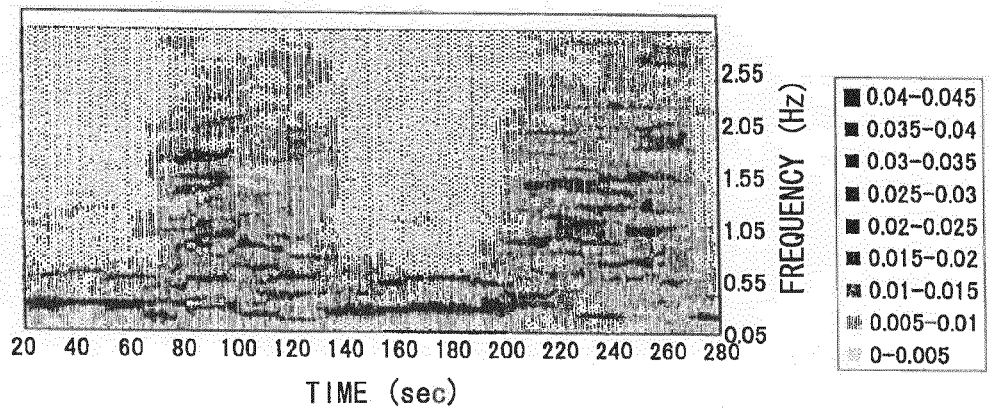
FIG. 19B is a graph showing frequency analysis results thereof.

Next, a test was conducted regarding a possibility of obtaining voice signals obtained from the air cushions 10. In this test, the subject was tested while seated on the seat 300 of the above test example 1 in a resting state for a predetermined time. In the test, after seated in a resting state for a predetermined time, reading of a book aloud for 60 seconds was repeated. Results are shown in FIG. 19. FIG. 19A shows a time-series original waveform obtained from the air cushions 10. From this graph, a large amplitude variation is seen in the original waveform when reading aloud. FIG. 19B shows frequency analysis results, in which there is a peak at 0.3 Hz in a state of not reading aloud where it is possible to detect breath components, and meanwhile the frequency while reading aloud is a higher frequency. Consequently, it was found that voice signals can be sampled with the air cushions 10.

On the other hand, FIG. 20 show time-series original waveforms obtained from the air cushions 10 when three subjects (FIG. 20A is of a male in his thirties (middle to high voice), FIG. 20B is of a male in his twenties (low voice), FIG. 20C is of a female in her twenties (thin and high voice)) read the Japanese syllabary aloud between 30 seconds and 40 seconds, and hum a song between 50 seconds and 60 seconds. From these graphs, it can be seen that the waveform between 30 seconds and 40 seconds and the waveform between 50 seconds and 60 seconds when a voice was produced are different prominently before and after these periods. Further, it can also be seen that how amplitude changes is different depending on the voice range of each subject. Moreover, from these points, it can be presumed that the output of air pressure variation in the air cushions 10 due to propagation of sound is different between when the muscles are tensed and when they are relaxed. Therefore, from an air pressure variation accompanying a voice, it can be estimated which of the sympathetic nervous system and the parasympathetic nervous system is more active. As a consequence, it is possible to further estimate the state of LF/HF which is index of sympathetic nervous system activity of heartbeats and the state of HF which is an index of parasympathetic nervous system activity.

Test Example 6

Next, a method to separate breath components from an air pressure variation obtained from the air cushions 10 and estimate a time-series waveform of heartbeat components using a time-series waveform of the breath components will be described.

First of all, it is assumed that a time-series waveform ($g_1(t)$) and a frequency component ($G_1(F)$) of breath components obtained from an air pressure variation in the air cushions 10 as well as a frequency response function (TF) of heartbeat components with respect to the breath components are known variables, and a time-series waveform ($g_2(t)$) and a frequency component ($G_2(F)$) of heartbeat components are unknown variables.

In this case, the frequency component of the heartbeat components can be obtained from $G_2(F)=TF \cdot G_1(F)=A_1A_3-B_1B_3+(A_1A_3+B_1B_3)j$ Then the time-series waveform ($g_2(t)$) of the heartbeat components is obtained by inverse Fourier transforming (IFFT) the frequency component ($G_2(F)$) of the heartbeat components, and consequently, it becomes possible to estimate the time-series waveform of the heartbeat components from the time-series waveform of the breath components.

Here, A is a real part and B is an imaginary part.

A frequency response function (TF) of heartbeat components with respect to breath components is represented as:

$$TF = G_2(F)/G_1(F)$$
$$= (A_2 + B_2 j)/(A_1 + B_1 j)$$
$$= [A_1A_2 + B_1B_2 + (A_1B_2 - A_2B_1)j]/(A_1^2 + B_1^2)$$
$$= A_3 + B_3 j$$

where $A_3=(A_1A_2+B_1B_2)/(A_1^2)$, $B_3=(A_1B_2-A_2B_1)/A_1^2+B_1^2)$.

Further, the frequency response function (TF) has bilateral characters of amplitude characteristic (magnitude) and phase characteristic ($\theta$), and given by:

[Equation 1]

amplitude characteristic (magnitude)=$\sqrt{A_3^2+B_3^2}$, and

[Equation 2]

phase characteristic ($\theta$)=$\tan^{-1}(B_3/A_3)$.

Then, the amplitude characteristic and the phase characteristic are obtained from actually measured data, and the frequency response function (TF) is defined.

In this example, from each of 20 male and female subjects, the time-series waveform of breath components was measured from the air cushions 10, the amplitude characteristic and the phase characteristic were obtained, and average values thereof were further calculated using the above equations. Data of average values are shown in FIG. 21A and FIG. 21B, and these FIG. 21A and FIG. 21B were defined as the frequency response function (TF).

Thus, it is possible to estimate the time-series waveform and the frequency component of heartbeat components from the time-series waveform of breath components. In addition, as estimation means of heartbeat components, other than the means using Fourier transform and using the frequency response functions (TF) of FIG. 21A and FIG. 21B as described above, it is also possible to use an analysis technique by wavelet transform.

The obtained data of heartbeat components can be used for presuming the aforementioned hypnagogic symptoms. For instance, FIG. 22 shows graphs showing calculation of the gradient of a frequency relative to a time axis from time-series changes of the frequency relative to the time axis. This technique is similar to the technique of calculating the gradient of power values and the gradient of maximum Lyapunov indexes described in the test example 3. First, peaks are detected from a time-series waveform, and peak intervals are defined as T1, T2, T3, and so on. Next, by the peak intervals, a variation waveform of a frequency is created. At this time, F and T are represented by a relationship of F=1/T.

Next, from the variation waveform of the frequency, gradient components are calculated using least square method for a time width Tw (180 seconds). Then, an overlapping time is slid by an overlap time (Rap (162 seconds)), and gradient components are calculated sequentially by least square method, the time series of the gradients of the frequency is created.

Consequently, variation tendencies of frequencies can be seen. For example, for a variation tendency of a frequency of heartbeat components, it is possible to further estimate the state of LF/HF which is index of sympathetic nervous system activity of heartbeats and the state of HF which is an index of parasympathetic nervous system activity, by determining which of LF and HF this value belongs, similarly to the test example 5.

Test Example 7

Figure 23:
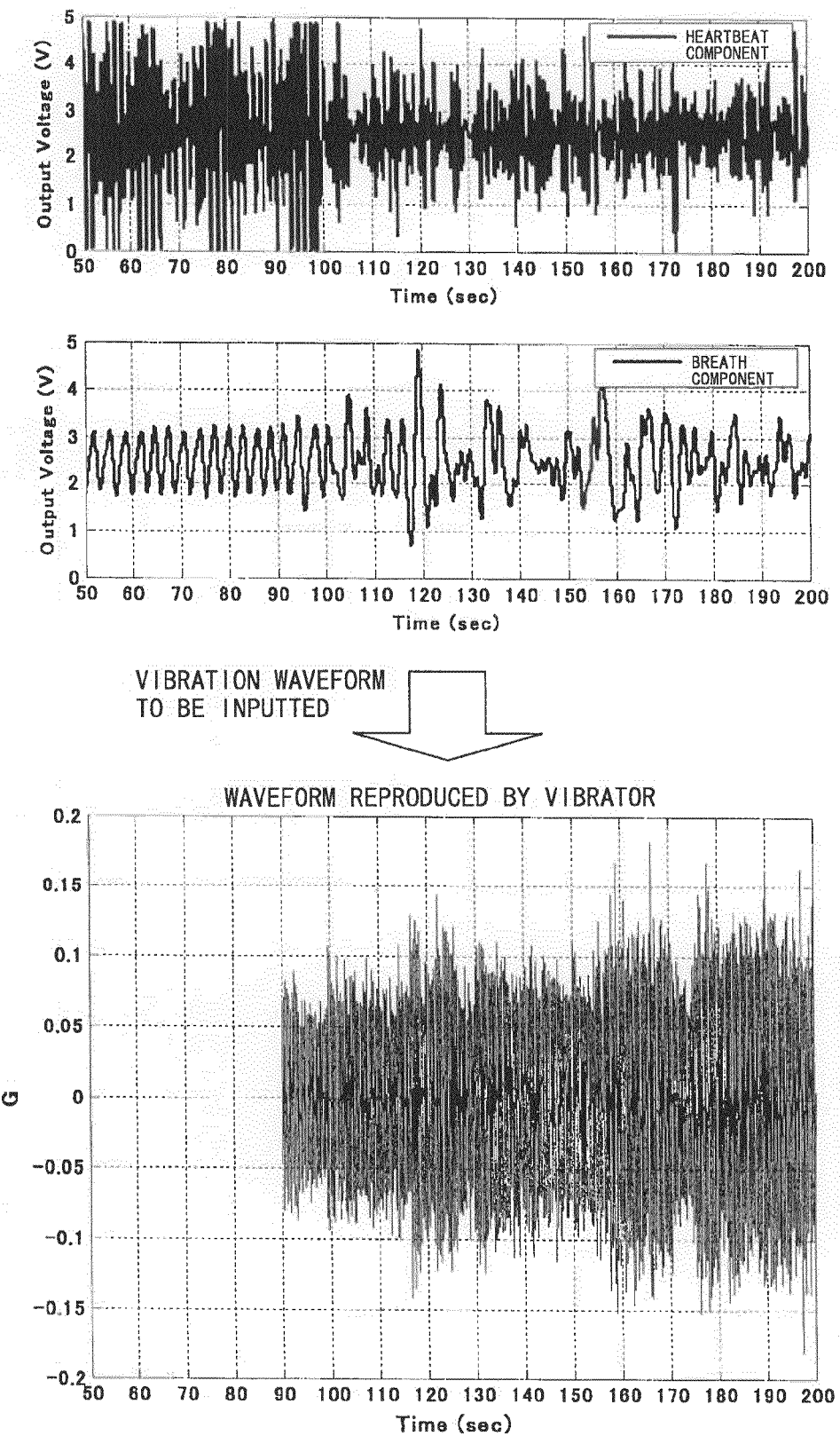
FIG. 23 shows graphs showing results of one subject of test example 7.
Figure 24:
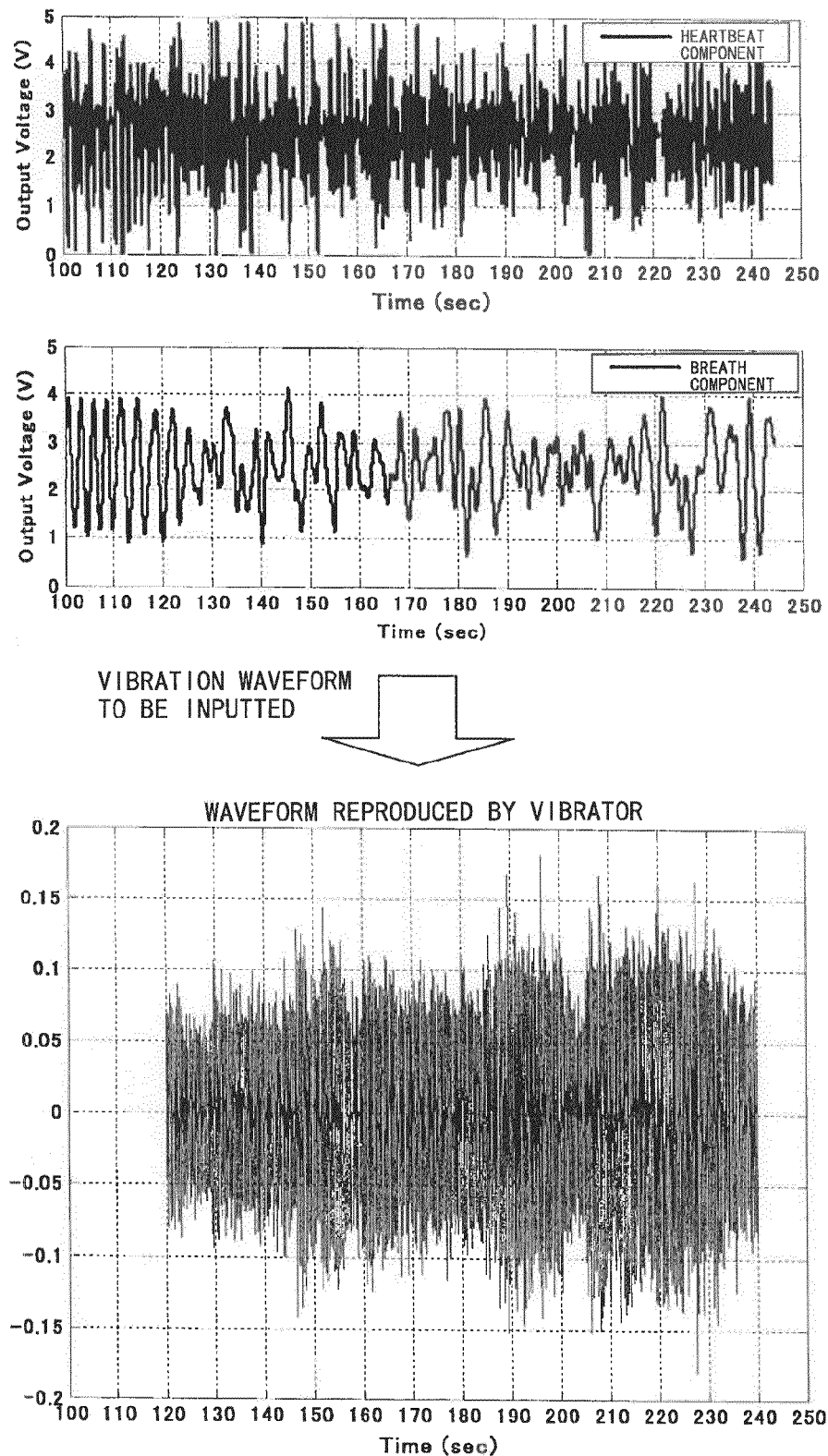
FIG. 24 shows graphs showing results of another subject of test example 7.
Figure 25:
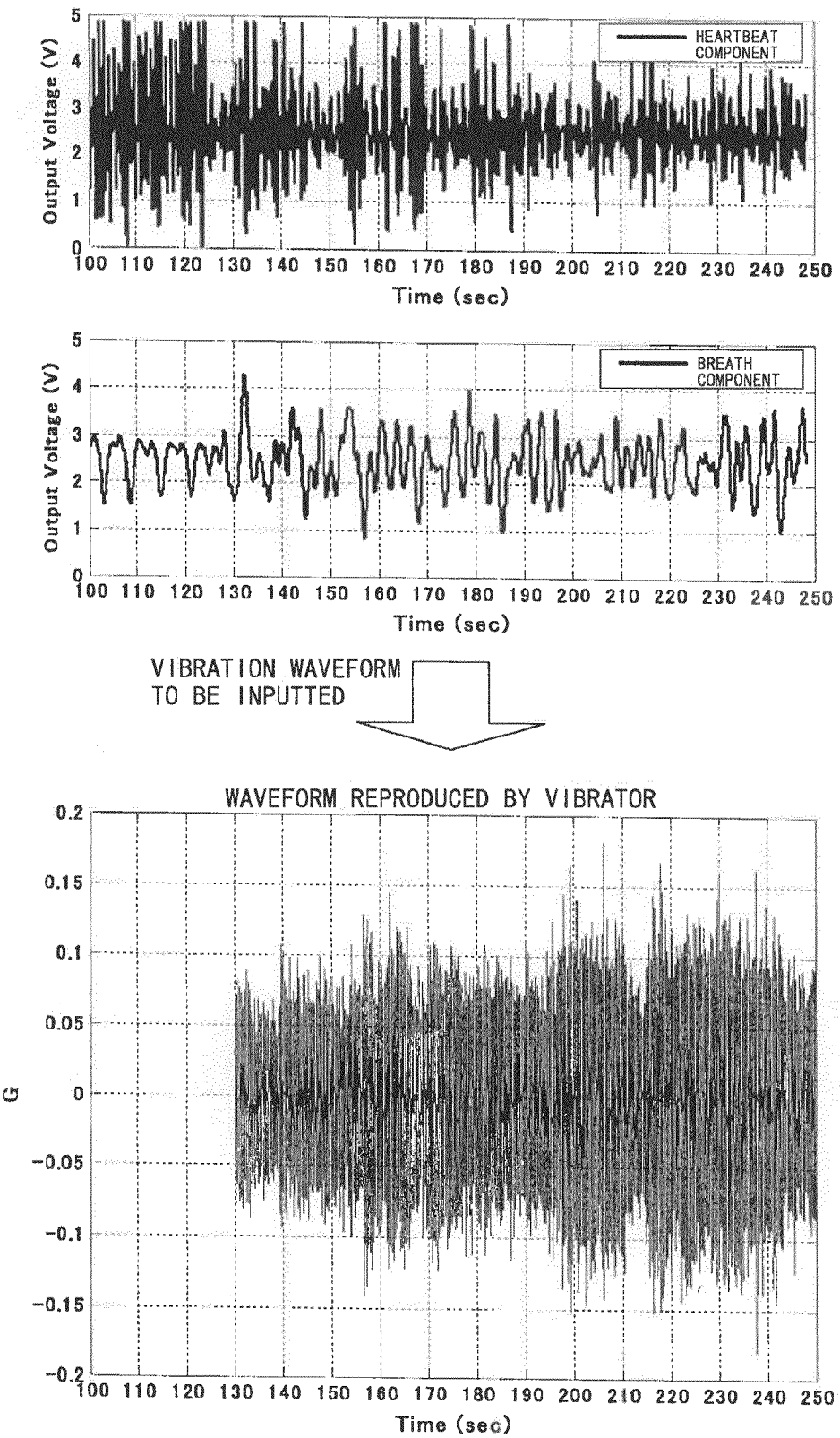
FIG. 25 shows graphs showing results of still another subject of test example 7.

Next, three healthy Japanese male subjects in their twenties to thirties ("asano" (FIG. 23), "ochiai" (FIG. 24), and "maeda" (FIG. 25)) were seated, vibration with a random waveform was applied in the middle by a vibrator, and time-series waveforms of heartbeat components and breath components during vibration were compared. FIG. 23 to FIG. 25 show results, in each of which the lowest graph shows operation timing of the vibrator and a vibration waveform, and shows time-series waveforms of breath components and heartbeat components for the measurement time corresponding to them. These time-series waveforms are time-series signals which are filtered through the analog signal processing circuit and thereafter separated into breath components and heartbeat components, and are data before calculating gradients of them similar to the test example 3.

Looking into FIG. 23 to FIG. 25, it can be seen that all the subjects presented stable waveforms of heartbeat components and breath components before the vibration is inputted, but after the vibration is inputted, fluctuations change in both the heartbeat components and the breath components according to the magnitude of the vibration. The magnitude of fluctuation due to the magnitude of vibration differs among individuals and is not constant. For example, in the case of the subject in FIG. 23, the fluctuation in the heartbeat components becomes small just after the vibration is inputted, and the fluctuation in the breath components becomes large just after the vibration is input. Moreover, at 170 seconds and thereafter where the vibration increases, the fluctuation in breath components of this subject becomes small. In any case, it can be known that, just by looking at this time-series waveform detected by the air cushions 10 of the present invention, a fluctuation different from the preceding fluctuation and the load increases by the input of vibration. Therefore, before calculating the gradient time series, a change in human condition can be detected quickly by analyzing the time-series waveform at this time.

Regarding the subjects in FIG. 24 and FIG. 25, similarly, there occurs a change in fluctuations of both heartbeat components and breath components after the input of vibration. However, regarding breath components, these two subjects have a fluctuation which increases gradually at 220 seconds and thereafter where the fluctuations become large, and it can be seen that they have different responses from the subject of FIG. 23. From these results, it is possible that individual differences can be detected by time-series waveforms.

FIG. 26 to FIG. 28 show time-series waveforms of heartbeat components and breath components of the respective subjects of FIG. 23 to FIG. 25 in a static state in the morning, at noon, and at night. From the time-series waveforms, it can be seen that there is a significant difference in fluctuations of heartbeat components and breath components even in the same person due to circadian rhythm. For example, the subject ("asano") in FIG. 26 has a large fluctuation in the morning, and thus it can be read that this person is not a morning person, and becomes more stable toward the night. Similarly, it can be read that the subject ("ochiai") in FIG. 27 tends to be stable almost all day, and the subject ("maeda") in FIG. 28 is not a morning person either.

Figure 29A:
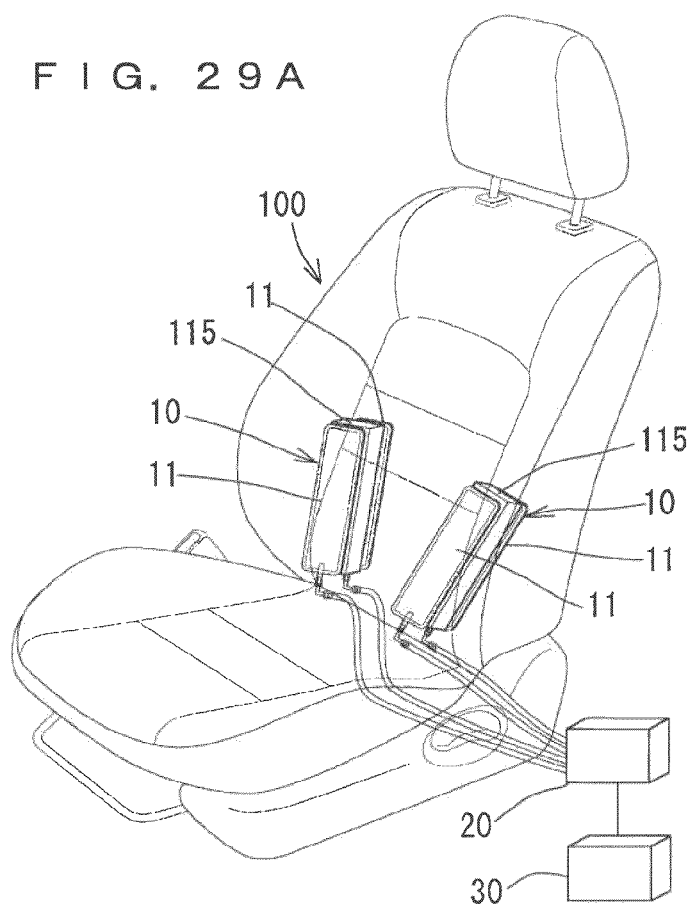
FIG. 29 is a view for describing the structure of an air cushion in which a buffer material (three-dimensional solid knitted fabric and viscoelastic urethane) for damping vibration is sandwiched between the two air bags.
Figure 29B:
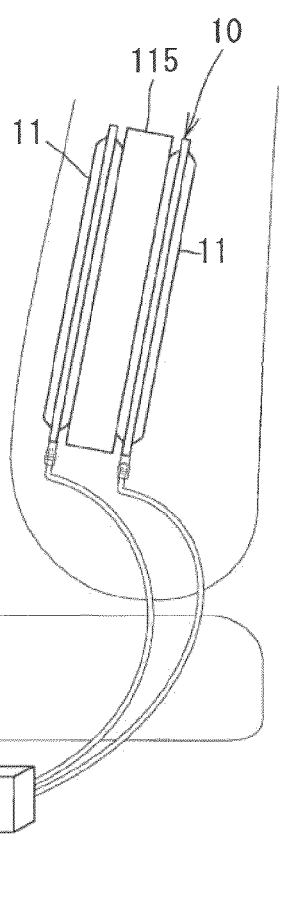
Figure 30A:
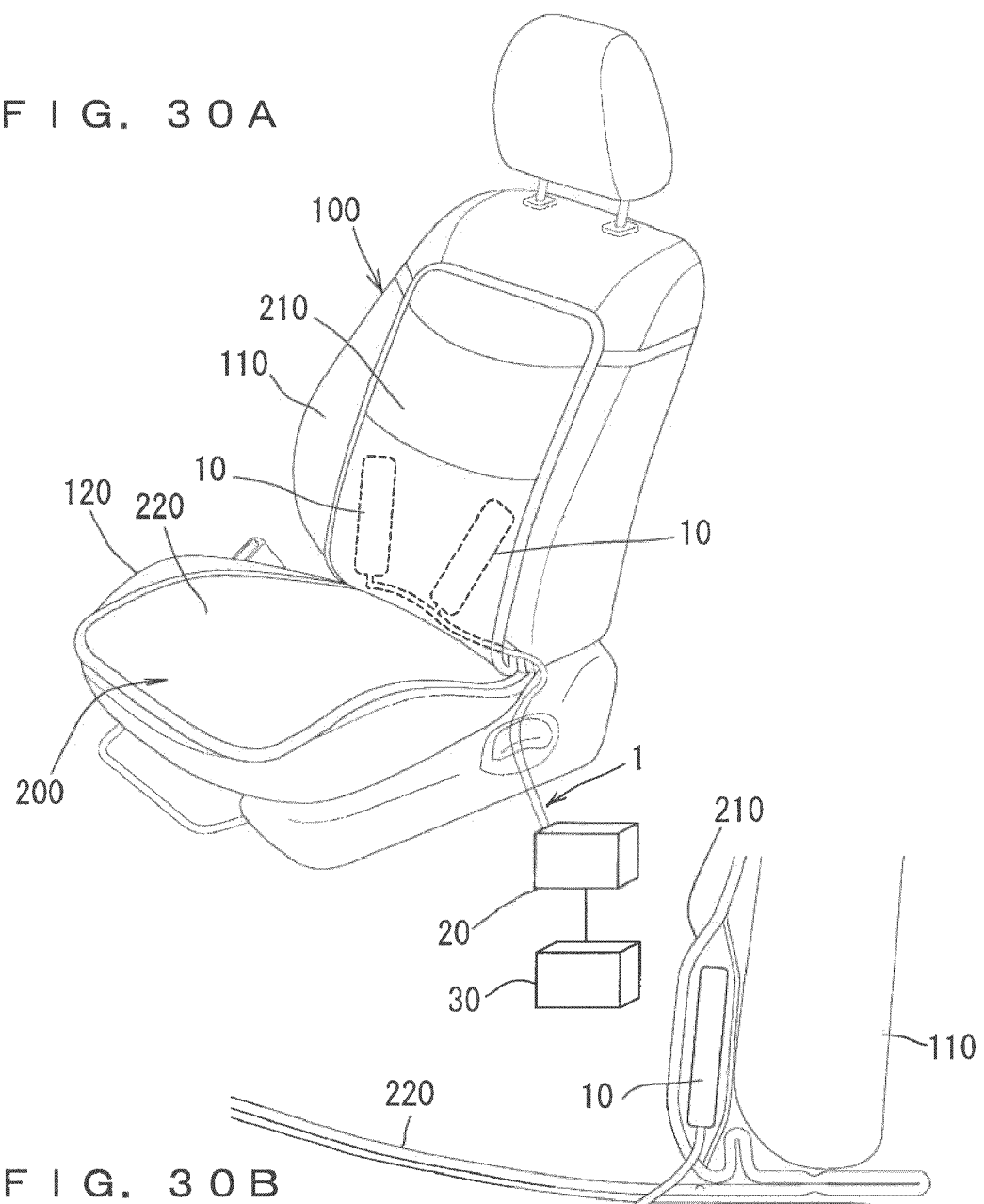
FIG. 30A is a view showing an embodiment in which air cushions are incorporated in an auxiliary cushion (cushion for seat)
Figure 30B:
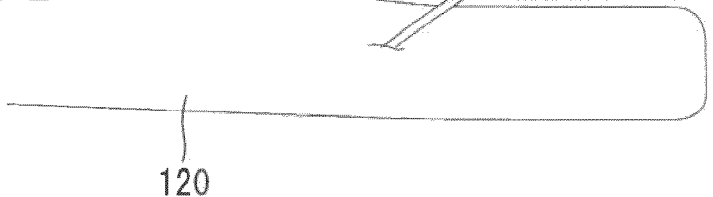
FIG. 30B is a partial cross-sectional view of FIG. 30A.

Noted that in the above embodiment, although the air cushions 10 each having two air bags 11, 11 and being folded in two are used, it may be arranged that two air bags 11, 11 not connected to each other are stacked and used. Further, as shown in FIG. 29, it may be arranged that a buffer material (three-dimensional solid knitted fabric and viscoelastic urethane) 115 for damping vibration is sandwiched between the two air bags 11, 11. Further, in the above embodiment, the air cushions 10 are incorporated in the seat back of the seat 100, but as shown in FIG. 30 it is not limited to the seat fixed in a vehicle such as automobile or train. It can be arranged that the air cushions 10 are attached to a seat back 210 of an auxiliary cushion (cushion for seat) 200, which integrally includes a seat cushion 220 and the seat back 210 to be used by mounting on such a seat, and is capable of being bent from the boundary of the both. Note that the meaning of the "seat" in the present specification and claims also includes such an auxiliary cushion (cushion for seat) 200.

The invention claimed is:

1. A bio-signal analyzer, comprising:
a pair of air cushions each having an air bag formed by sealing except an air inlet/outlet port and a resilience applying member, which applies resilience in an expansion direction to the air bag when air is exhausted from the inlet/outlet port by pressing with a load, and which allows air to enter the air bag through the inlet/outlet port accompanying decrease of the load, the air cushions being incorporated in portions supporting a vicinity of a lumbar region of a person in a human body support means;
an air pressure measuring instrument connected to the inlet/outlet port of each of the air cushions to detect an air pressure variation in each of the air cushions caused by a human bio-signal; and
an analyzing means that receives an electric signal of the air pressure variation in each of the air cushions detected by the air pressure measuring instrument to analyze a human condition,
wherein each of the air cushions is disposed at one of positions corresponding respectively to left and right iliocostalis lumborum muscles of the person, in a substantially vertically long state along the respective iliocostalis lumborum muscles, and has a length such that an upper end thereof is set at least at a height corresponding to a lower face of a human diaphragm, and
wherein the resilience applying member includes a three-dimensional solid knitted fabric which is accommodated in the air bag and which applies resilience to the air bag from inside.

2. The bio-signal analyzer according to claim 1, wherein the length of each air cushion is in a range of 150 mm to 300 mm.

3. The bio-signal analyzer according to claim 1, wherein each air cushion comprises two air bags, and is structured such that the two air bags overlap each other.

4. The bio-signal analyzer according to claim 3, wherein the analyzing means is configured to perform analysis using a sum of values of respective air pressure variations of the two air bags of each air cushion.

5. A seat, comprising:
air cushions incorporated in a portion supporting a vicinity of a lumbar region in a seat back,
wherein the air cushions each include an air bag formed by sealing except an air inlet/outlet port and a resilience applying member, which applies resilience in an expansion direction to the air bag when air is exhausted from the inlet/outlet port by pressing with a load, and which allows air to enter the air bag through the inlet/outlet port accompanying decrease of the load,
wherein the resilience applying member includes a three-dimensional solid knitted fabric which is accommodated in the air bag and which applies resilience to the air bag from inside,
wherein the air cushions are disposed in a pair at portions corresponding respectively to left and right iliocostalis lumborum muscles of a person, in a substantially vertically long state along the respective iliocostalis lumborum muscles, such that upper ends thereof are set at least at a height corresponding to a lower face of a human diaphragm, and
wherein the seat further comprises an air pressure measuring instrument connected to the inlet/outlet ports of each air cushion that detects an air pressure variation in each of the air cushions caused by a human bio-signal and that transmits the air pressure variation to an analyzing means.

6. The seat according to claim 5, wherein a length of the air cushions is in a range of 150 mm to 300 mm.

7. The seat according to claim 6, wherein the air cushions are disposed so that respective inside lower ends of the air cushions are located in ranges of 20 mm to 80 mm leftward and rightward respectively from a center of the seat back forming the seat and in a range of 10 mm to 80 mm upward along the seat back from a boundary between a seat cushion and the seat back.

8. The seat according to claim 7, wherein the air cushions are disposed so that respective inside upper ends of the air cushions are located in ranges of 40 mm to 100 mm leftward and rightward respectively from the center of the seat back and separated from the center of the seat back farther than the inside lower ends.

9. The seat according to claim 5, wherein the air cushions each comprise two air bags, and is structured such that the two air bags overlap each other.

10. The seat according to claim 9, wherein the analyzing means is configured to perform analysis using a sum of values of respective air pressure variations of the two air bags of the air cushions.

11. The seat according to claim 5, wherein the analyzing means analyzes a human condition from the air pressure variation in the air cushions generated by a human bio-signal, the analyzing means being attached to a portion of one of a seat cushion and the seat back.

12. A bio-signal analyzing method using air cushions incorporated in portions supporting a vicinity of a lumbar region in a seat back, the method comprising:
  using, as each of the air cushions, an air cushion having an air bag formed by sealing except an air inlet/outlet port and a resilience applying member, which applies resilience in an expansion direction to the air bag when air is exhausted from the inlet/outlet port by pressing with a load, and which allows air to enter the air bag through the inlet/outlet port accompanying decrease of the load, the resilience applying member including a three-dimensional solid knitted fabric which is accommodated in the air bag and applies resilience to the air bag from inside;
  setting the air cushions in a pair at positions corresponding respectively to left and right iliocostalis lumborum muscles of a person, in a substantially vertically long state along the iliocostalis lumborum muscles, upper ends thereof being at least at a height corresponding to a lower face of a human diaphragm; and
  detecting an air pressure variation in each of the air cushions generated by a breath, a heartbeat, or a voice as a bio-signal, the air pressure variation being detected by an air pressure measuring instrument connected to the inlet/outlet port of each of the air cushions to transmit an electric signal corresponding to the air pressure variation to an analyzing means, the analyzing means determining a biological state.

* * * * *